(12) United States Patent
Cho

(10) Patent No.: US 12,201,753 B2
(45) Date of Patent: Jan. 21, 2025

(54) LOW TEMPERATURE, NANOSTRUCTURED CERAMIC COATINGS

(71) Applicant: The Research Foundation for The State University of New York, Binghamton, NY (US)

(72) Inventor: Junghyun Cho, Vestal, NY (US)

(73) Assignee: The Research Foundation for The State University of New York, Binghamton, NY (US)

( * ) Notice: Subject to any disclaimer, the term of this patent is extended or adjusted under 35 U.S.C. 154(b) by 753 days.

(21) Appl. No.: 17/093,382

(22) Filed: Nov. 9, 2020

(65) Prior Publication Data

US 2021/0213177 A1 Jul. 15, 2021

Related U.S. Application Data

(62) Division of application No. 14/734,520, filed on Jun. 9, 2015, now Pat. No. 10,828,400.

(60) Provisional application No. 62/010,006, filed on Jun. 10, 2014.

(51) Int. Cl.
| | |
|---|---|
| A61L 31/08 | (2006.01) |
| A61L 29/10 | (2006.01) |
| A61L 29/16 | (2006.01) |
| A61L 31/16 | (2006.01) |
| C02F 1/32 | (2023.01) |
| C02F 1/72 | (2023.01) |
| C08J 7/06 | (2006.01) |
| C08J 7/14 | (2006.01) |
| C25D 9/04 | (2006.01) |
| B01J 35/39 | (2024.01) |
| B29C 35/08 | (2006.01) |
| B29C 59/14 | (2006.01) |

(52) U.S. Cl.
CPC .......... *A61L 31/088* (2013.01); *A61L 29/106* (2013.01); *A61L 29/16* (2013.01); *A61L 31/16* (2013.01); *C02F 1/325* (2013.01); *C02F 1/725* (2013.01); *C08J 7/06* (2013.01); *C08J 7/14* (2013.01); *C25D 9/04* (2013.01); *A61L 2300/404* (2013.01); *B01J 35/39* (2024.01); *B29C 2035/0827* (2013.01); *B29C 59/14* (2013.01); *C02F 2201/326* (2013.01); *C02F 2303/02* (2013.01); *C02F 2305/08* (2013.01); *C02F 2305/10* (2013.01); *C02F 2307/12* (2013.01); *C08J 2323/22* (2013.01); *C08J 2331/04* (2013.01); *C08J 2383/04* (2013.01); *C08J 2389/00* (2013.01); *Y10T 428/265* (2015.01); *Y10T 442/2525* (2015.04)

(58) Field of Classification Search
CPC ...... A61L 31/088; A61L 31/16; A61L 29/106; A61L 29/16; C02F 1/325; C02F 1/725; C25D 9/04

USPC ......................................................... 442/123
See application file for complete search history.

(56) References Cited

U.S. PATENT DOCUMENTS

| | | | |
|---|---|---|---|
| 6,350,397 | B1 | 2/2002 | Heikkila et al. |
| 6,537,517 | B1 | 3/2003 | Kasuga et al. |
| 6,764,796 | B2 | 7/2004 | Fries |
| 6,846,565 | B2 | 1/2005 | Korgel et al. |
| 6,918,946 | B2 | 7/2005 | Korgel et al. |
| 7,019,391 | B2 | 3/2006 | Tran |
| 7,071,139 | B2 | 7/2006 | Gole |
| 7,186,392 | B2 | 3/2007 | Gole |
| 7,229,600 | B2 | 6/2007 | Yadav |
| 7,232,556 | B2 | 6/2007 | Yadav |
| 7,285,188 | B2 | 10/2007 | Gole |
| 7,312,087 | B2 | 12/2007 | Duong et al. |
| 7,330,369 | B2 | 2/2008 | Tran |
| 7,335,908 | B2 | 2/2008 | Samuelson et al. |
| 7,354,850 | B2 | 4/2008 | Seifert et al. |
| 7,375,417 | B2 | 5/2008 | Tran |
| 7,393,699 | B2 | 7/2008 | Tran |
| 7,432,522 | B2 | 10/2008 | Samuelson et al. |
| 7,476,607 | B2 | 1/2009 | Yamada et al. |
| 7,482,382 | B2 | 1/2009 | Li et al. |
| 7,489,537 | B2 | 2/2009 | Tran |
| 7,491,431 | B2 | 2/2009 | Chiruvolu et al. |
| 7,498,005 | B2 | 3/2009 | Yadav |
| 7,521,394 | B2 | 4/2009 | Xie et al. |
| 7,524,370 | B1 | 4/2009 | Terada et al. |
| 7,528,002 | B2 | 5/2009 | Samuelson et al. |
| 7,541,509 | B2 | 6/2009 | Sigmund et al. |
| 7,572,400 | B2 | 8/2009 | Fujikawa et al. |
| 7,575,784 | B1 | 8/2009 | Bi et al. |
| 7,601,326 | B2 | 10/2009 | Torardi |
| 7,601,327 | B2 | 10/2009 | Torardi |
| 7,608,147 | B2 | 10/2009 | Samuelson et al. |
| 7,630,227 | B2 | 12/2009 | Tran |
| 7,645,397 | B2 | 1/2010 | Parce et al. |
| 7,655,274 | B2 | 2/2010 | Remington |
| 7,670,581 | B2 | 3/2010 | Korgel et al. |
| 7,677,198 | B2 | 3/2010 | Cheng et al. |
| 7,682,943 | B2 | 3/2010 | Samuelson et al. |
| 7,687,431 | B2 | 3/2010 | Nakayama et al. |
| 7,695,689 | B2 | 4/2010 | Nakamura et al. |
| 7,713,955 | B2 | 5/2010 | Whiteford et al. |
| 7,722,953 | B2 | 5/2010 | Korgel et al. |
| 7,745,813 | B2 | 6/2010 | Samuelson et al. |

(Continued)

*Primary Examiner* — Vincent Tatesure

(74) *Attorney, Agent, or Firm* — Hoffberg & Associates; Steven M. Hoffberg

(57) ABSTRACT

A substrate subject to degradation at temperatures above 100° C. is coated with a nanostructured ceramic coating having a thickness in excess of 100 nm, formed on a surface of the substrate, wherein a process temperature for deposition of the nanostructured coating does not exceed 90° C. The coating may be photocatalytic, photovoltaic, or piezoelectric. The coating, when moistened and exposed to ultraviolet light or sunlight, advantageously generates free radicals, which may be biocidal, deodorizing, or assist in degradation of surface deposits on the substrate after use. The substrate may be biological or organic, and may have a metallic or conductive intermediate layer.

19 Claims, No Drawings

(56) References Cited

U.S. PATENT DOCUMENTS

| | | |
|---|---|---|
| 7,763,149 B2 | 7/2010 | Maggard |
| 7,826,336 B2 | 11/2010 | Thelander et al. |
| 7,846,864 B2 | 12/2010 | Ham et al. |
| 7,864,560 B2 | 1/2011 | Tran |
| 7,883,610 B2 | 2/2011 | Monzyk et al. |
| 7,901,660 B2 | 3/2011 | Xie et al. |
| 7,910,492 B2 | 3/2011 | Samuelson et al. |
| 7,911,035 B2 | 3/2011 | Seifert et al. |
| 7,927,567 B2 | 4/2011 | Yamanaka et al. |
| 7,931,683 B2 | 4/2011 | Weber et al. |
| 7,938,855 B2 | 5/2011 | Gregorich et al. |
| 7,942,926 B2 | 5/2011 | Benco et al. |
| 7,960,260 B2 | 6/2011 | Samuelson et al. |
| 7,973,997 B2 | 7/2011 | Lee |
| 7,976,915 B2 | 7/2011 | Scheuermann et al. |
| 7,977,402 B2 | 7/2011 | Madhusoodhanan et al. |
| 7,981,150 B2 | 7/2011 | Scheuermann et al. |
| 7,988,947 B2 | 8/2011 | Torardi |
| 7,994,422 B2 | 8/2011 | Jin et al. |
| 8,002,823 B2 | 8/2011 | Kuehling |
| 8,003,563 B2 | 8/2011 | Sato et al. |
| 8,029,554 B2 | 10/2011 | Holman et al. |
| 8,048,523 B2 | 11/2011 | Kambe et al. |
| 8,049,203 B2 | 11/2011 | Samuelson et al. |
| 8,066,763 B2 | 11/2011 | Alt |
| 8,067,054 B2 | 11/2011 | Weber |
| 8,067,299 B2 | 11/2011 | Samuelson et al. |
| 8,067,402 B2 | 11/2011 | Whiteford et al. |
| 8,067,403 B2 | 11/2011 | Whiteford et al. |
| 8,070,797 B2 | 12/2011 | Flanagan et al. |
| 8,071,156 B2 | 12/2011 | Weber et al. |
| 8,076,846 B2 | 12/2011 | Mizuno et al. |
| 8,084,762 B2 | 12/2011 | Tran |
| 8,089,681 B2 | 1/2012 | Wu et al. |
| 8,120,009 B2 | 2/2012 | Samuelson et al. |
| 8,163,084 B2 | 4/2012 | Terada et al. |
| 8,163,633 B2 | 4/2012 | Korgel et al. |
| 8,178,122 B2 | 5/2012 | Bignozzi et al. |
| 8,183,587 B2 | 5/2012 | Samuelson et al. |
| 8,187,620 B2 | 5/2012 | Chandrasekaran et al. |
| 8,216,632 B2 | 7/2012 | Schoenle et al. |
| 8,221,655 B2 | 7/2012 | Torardi |
| 8,221,822 B2 | 7/2012 | Flanagan et al. |
| 8,227,817 B2 | 7/2012 | Pedersen et al. |
| 8,231,980 B2 | 7/2012 | Atanasoska et al. |
| 8,242,481 B2 | 8/2012 | Samuelson et al. |
| 8,247,680 B2 | 8/2012 | Inagaki et al. |
| 8,268,381 B2 | 9/2012 | Whiteford et al. |
| 8,269,214 B2 | 9/2012 | Smigelski, Jr. et al. |
| 8,277,631 B2 | 10/2012 | Eastman et al. |
| 8,283,412 B2 | 10/2012 | Liu et al. |
| 8,287,937 B2 | 10/2012 | Radhakrishnan et al. |
| 8,318,126 B2 | 11/2012 | Wong et al. |
| 8,318,297 B2 | 11/2012 | Tian et al. |
| 8,320,514 B2 | 11/2012 | Okamura et al. |
| 8,323,982 B2 | 12/2012 | LeBoeuf et al. |
| 8,344,238 B2 | 1/2013 | Gronet et al. |
| 8,353,949 B2 | 1/2013 | Weber et al. |
| 8,357,954 B2 | 1/2013 | Samuelson et al. |
| 8,376,013 B2 | 2/2013 | Bourke, Jr. et al. |
| 8,377,414 B2 | 2/2013 | Torardi |
| 8,389,958 B2 | 3/2013 | Vo-Dinh et al. |
| 8,403,239 B2 | 3/2013 | Kusuura |
| 8,415,556 B2 | 4/2013 | Singh et al. |
| 8,425,803 B2 | 4/2013 | Parce et al. |
| 8,426,817 B2 | 4/2013 | Ravichandran et al. |
| 8,431,149 B2 | 4/2013 | McMorrow et al. |
| 8,432,604 B2 | 4/2013 | Lee |
| 8,440,162 B1 | 5/2013 | Wong et al. |
| 8,449,603 B2 | 5/2013 | Weber et al. |
| 8,450,716 B2 | 5/2013 | Tran |
| 8,450,717 B1 | 5/2013 | Samuelson et al. |
| 8,455,857 B2 | 6/2013 | Samuelson et al. |
| 8,541,337 B2 | 9/2013 | Xie et al. |
| 8,574,419 B2 | 11/2013 | Phamhuu et al. |
| 8,574,615 B2 | 11/2013 | Tenney et al. |
| 8,585,627 B2 | 11/2013 | Dacey, Jr. et al. |
| 8,592,037 B2 | 11/2013 | Parce et al. |
| 8,598,266 B2 | 12/2013 | Xu |
| 8,609,205 B2 | 12/2013 | Hu et al. |
| 8,618,212 B2 | 12/2013 | Liu et al. |
| 8,618,509 B2 | 12/2013 | Vo-Dinh et al. |
| 8,618,595 B2 | 12/2013 | Korgel et al. |
| 8,624,105 B2 | 1/2014 | Routkevitch et al. |
| 8,628,726 B2 | 1/2014 | Pham-Huu et al. |
| 8,629,076 B2 | 1/2014 | Worsley et al. |
| 8,632,663 B2 | 1/2014 | Yoshida et al. |
| 8,647,292 B2 | 2/2014 | Dacey, Jr. et al. |
| 8,647,915 B2 | 2/2014 | Aytug et al. |
| 8,652,409 B2 | 2/2014 | LeBoeuf et al. |
| 8,652,874 B2 | 2/2014 | Wang et al. |
| 8,653,497 B2 | 2/2014 | Tran |
| 8,663,380 B2 | 3/2014 | Akhtar et al. |
| 8,664,143 B2 | 3/2014 | Worsley et al. |
| 8,669,325 B1 | 3/2014 | Hyman |
| 8,679,580 B2 | 3/2014 | Lu et al. |
| 8,681,925 B2 | 3/2014 | Okamura et al. |
| 8,702,640 B2 | 4/2014 | Dacey, Jr. et al. |
| 8,706,211 B2 | 4/2014 | Dacey, Jr. et al. |
| 8,731,132 B2 | 5/2014 | Okamura et al. |
| 8,734,718 B2 | 5/2014 | Dacey, Jr. et al. |
| 8,748,111 B2 | 6/2014 | Mershin et al. |
| 8,753,304 B2 | 6/2014 | Dacey, Jr. et al. |
| 8,771,343 B2 | 7/2014 | Weber et al. |
| 8,772,626 B2 | 7/2014 | Samuelson et al. |
| 8,779,277 B2 | 7/2014 | Inagaki et al. |
| 8,790,462 B2 | 7/2014 | Samuelson et al. |
| 8,790,614 B2 | 7/2014 | Richards et al. |
| 8,796,119 B2 | 8/2014 | Samuelson et al. |
| 8,796,417 B2 | 8/2014 | Shiba et al. |
| 8,796,544 B2 | 8/2014 | Mershin et al. |
| 8,815,273 B2 | 8/2014 | Atanasoska et al. |
| 8,815,275 B2 | 8/2014 | Zhou |
| 8,840,863 B2 | 9/2014 | Yang et al. |
| 8,847,476 B2 | 9/2014 | Wang |
| 8,864,341 B2 | 10/2014 | Davis et al. |
| 8,865,113 B2 | 10/2014 | Shankman |
| 8,871,670 B2 | 10/2014 | Seebauer |
| 8,871,926 B1 | 10/2014 | Fan et al. |
| 8,878,157 B2 | 11/2014 | Wu et al. |
| 8,883,115 B2 | 11/2014 | Tian |
| 8,884,507 B2 | 11/2014 | Davis et al. |
| 8,888,731 B2 | 11/2014 | Dacey, Jr. et al. |
| 8,900,292 B2 | 12/2014 | Gregorich et al. |
| 8,916,064 B2 | 12/2014 | Liu et al. |
| 8,920,491 B2 | 12/2014 | Flanagan et al. |
| 8,921,473 B1 | 12/2014 | Hyman |
| 8,927,615 B2 | 1/2015 | Bourke, Jr. et al. |
| 8,932,346 B2 | 1/2015 | Kuehling et al. |
| 8,936,734 B2 | 1/2015 | Landry et al. |
| 8,975,205 B2 | 3/2015 | Smith et al. |
| 8,993,089 B2 | 3/2015 | Conolly et al. |
| 8,994,270 B2 | 3/2015 | Koo et al. |
| 9,004,131 B2 | 4/2015 | Bourke, Jr. et al. |
| 9,005,480 B2 | 4/2015 | Furuta et al. |
| 9,018,122 B2 | 4/2015 | Mao et al. |
| 9,023,308 B2 | 5/2015 | Shankman |
| 9,040,145 B2 | 5/2015 | Lyons et al. |
| 2003/0003300 A1 | 1/2003 | Korgel et al. |
| 2003/0034486 A1 | 2/2003 | Korgel |
| 2004/0144726 A1 | 7/2004 | Chmelka et al. |
| 2004/0156986 A1 | 8/2004 | Yadav |
| 2004/0224147 A1 | 11/2004 | Chou |
| 2005/0008861 A1 | 1/2005 | Yadav et al. |
| 2005/0031876 A1 | 2/2005 | Lu et al. |
| 2005/0126338 A1 | 6/2005 | Yadav |
| 2005/0191492 A1 | 9/2005 | Yadav |
| 2005/0218397 A1 | 10/2005 | Tran |
| 2005/0218398 A1 | 10/2005 | Tran |
| 2005/0230822 A1 | 10/2005 | Tran |
| 2005/0231855 A1 | 10/2005 | Tran |
| 2005/0260269 A1 | 11/2005 | Engelbrecht et al. |
| 2005/0265935 A1 | 12/2005 | Hollingsworth et al. |
| 2005/0266697 A1 | 12/2005 | Korgel et al. |

(56) References Cited

U.S. PATENT DOCUMENTS

| | | |
|---|---|---|
| 2005/0267345 A1 | 12/2005 | Korgel et al. |
| 2006/0102468 A1 | 5/2006 | Monzyk et al. |
| 2006/0118493 A9 | 6/2006 | Chmelka et al. |
| 2006/0133975 A1 | 6/2006 | Yamanaka et al. |
| 2006/0145326 A1 | 7/2006 | Tran |
| 2006/0182997 A1 | 8/2006 | Yamamoto et al. |
| 2006/0210798 A1 | 9/2006 | Burda |
| 2006/0240386 A1 | 10/2006 | Yaniv et al. |
| 2006/0243321 A1 | 11/2006 | Yamada et al. |
| 2006/0260674 A1 | 11/2006 | Tran |
| 2007/0000407 A1 | 1/2007 | Leong |
| 2007/0039814 A1 | 2/2007 | Maggard |
| 2007/0084507 A1 | 4/2007 | Noh et al. |
| 2007/0087187 A1 | 4/2007 | Lu et al. |
| 2007/0095389 A1 | 5/2007 | Cho et al. |
| 2007/0104629 A1 | 5/2007 | Yadav |
| 2007/0128707 A1 | 6/2007 | Rorrer et al. |
| 2007/0157967 A1 | 7/2007 | Mershin et al. |
| 2007/0181508 A1 | 8/2007 | Gui et al. |
| 2007/0202334 A1 | 8/2007 | Xie et al. |
| 2007/0202342 A1 | 8/2007 | Whiteford et al. |
| 2007/0218049 A1 | 9/2007 | Chen et al. |
| 2007/0285843 A1 | 12/2007 | Tran |
| 2008/0020127 A1 | 1/2008 | Whiteford et al. |
| 2008/0021212 A1 | 1/2008 | Whiteford et al. |
| 2008/0026041 A1 | 1/2008 | Tepper et al. |
| 2008/0031806 A1 | 2/2008 | Gavenonis et al. |
| 2008/0057420 A1 | 3/2008 | Inagaki et al. |
| 2008/0090930 A1 | 4/2008 | Madhusoodhanan et al. |
| 2008/0138267 A1 | 6/2008 | Yadav |
| 2008/0187684 A1 | 8/2008 | Hu et al. |
| 2008/0187724 A1 | 8/2008 | Fujikawa et al. |
| 2008/0207581 A1 | 8/2008 | Whiteford et al. |
| 2008/0220535 A1 | 9/2008 | LeBoeuf et al. |
| 2008/0239791 A1 | 10/2008 | Tran |
| 2008/0249600 A1 | 10/2008 | Atanasoska et al. |
| 2008/0283411 A1 | 11/2008 | Eastman et al. |
| 2008/0305045 A1 | 12/2008 | Kuniyil et al. |
| 2008/0318044 A1 | 12/2008 | Tian et al. |
| 2009/0005880 A1 | 1/2009 | Carinci et al. |
| 2009/0017303 A1 | 1/2009 | Choy et al. |
| 2009/0074649 A1 | 3/2009 | Korgel et al. |
| 2009/0104369 A1 | 4/2009 | Rajala et al. |
| 2009/0116277 A1 | 5/2009 | Tran |
| 2009/0126604 A1 | 5/2009 | Akhtar et al. |
| 2009/0188407 A1 | 7/2009 | Karvinen |
| 2009/0220600 A1 | 9/2009 | Parkin et al. |
| 2009/0220698 A1 | 9/2009 | Yadav |
| 2009/0270997 A1 | 10/2009 | Bignozzi et al. |
| 2009/0286936 A1 | 11/2009 | Ogata et al. |
| 2009/0294692 A1 | 12/2009 | Bourke, Jr. et al. |
| 2009/0311513 A1 | 12/2009 | Hu et al. |
| 2010/0000874 A1 | 1/2010 | Hinman et al. |
| 2010/0003204 A1 | 1/2010 | Loy et al. |
| 2010/0069229 A1 | 3/2010 | Yang et al. |
| 2010/0073995 A1 | 3/2010 | Tran |
| 2010/0190639 A1 | 7/2010 | Worsley et al. |
| 2010/0258446 A1 | 10/2010 | Mohapatra et al. |
| 2010/0261263 A1 | 10/2010 | Vo-Dinh et al. |
| 2010/0278720 A1 | 11/2010 | Wong et al. |
| 2010/0304204 A1 | 12/2010 | Routkevitch et al. |
| 2010/0307593 A1 | 12/2010 | Thimsen et al. |
| 2010/0308286 A1 | 12/2010 | Herlin et al. |
| 2010/0326699 A1 | 12/2010 | Greyling |
| 2011/0012096 A1 | 1/2011 | Carmeli et al. |
| 2011/0015300 A1 | 1/2011 | Whiteford et al. |
| 2011/0051220 A1 | 3/2011 | Lee |
| 2011/0053285 A1 | 3/2011 | Jeon et al. |
| 2011/0101862 A1 | 5/2011 | Koo et al. |
| 2011/0110141 A1 | 5/2011 | Tran |
| 2011/0123409 A1 | 5/2011 | Phamhuu et al. |
| 2011/0149400 A1 | 6/2011 | Miguez Garcia et al. |
| 2011/0171789 A1 | 7/2011 | Korgel et al. |
| 2011/0200761 A1 | 8/2011 | Kusuura |
| 2011/0208021 A1 | 8/2011 | Goodall et al. |
| 2011/0208023 A1 | 8/2011 | Goodall et al. |
| 2011/0208026 A1 | 8/2011 | Goodall et al. |
| 2011/0214996 A1 | 9/2011 | Yoshida et al. |
| 2011/0220855 A1 | 9/2011 | Weir et al. |
| 2011/0226738 A1 | 9/2011 | Lee |
| 2011/0238001 A1 | 9/2011 | Chen et al. |
| 2011/0245074 A1 | 10/2011 | Smith et al. |
| 2011/0245576 A1 | 10/2011 | Keller-Spitzer et al. |
| 2011/0262312 A1 | 10/2011 | Pham-Huu et al. |
| 2011/0275912 A1 | 11/2011 | Boyden et al. |
| 2011/0295088 A1 | 12/2011 | Boyden et al. |
| 2011/0295089 A1 | 12/2011 | Boyden et al. |
| 2011/0295090 A1 | 12/2011 | Boyden et al. |
| 2011/0297846 A1 | 12/2011 | Wang |
| 2012/0010314 A1 | 1/2012 | Charpentier et al. |
| 2012/0010481 A1 | 1/2012 | Goodall et al. |
| 2012/0040581 A1 | 2/2012 | Kim |
| 2012/0041285 A1 | 2/2012 | Goodall et al. |
| 2012/0041286 A1 | 2/2012 | Goodall et al. |
| 2012/0041287 A1 | 2/2012 | Goodall et al. |
| 2012/0066926 A1 | 3/2012 | Prabhakaran et al. |
| 2012/0077006 A1 | 3/2012 | Worsley et al. |
| 2012/0091429 A1 | 4/2012 | Tran |
| 2012/0091482 A1 | 4/2012 | Uchida et al. |
| 2012/0122652 A1 | 5/2012 | Worsley et al. |
| 2012/0122668 A1 | 5/2012 | Celiker et al. |
| 2012/0152336 A1 | 6/2012 | Cao et al. |
| 2012/0152337 A1 | 6/2012 | Aytug et al. |
| 2012/0164561 A1 | 6/2012 | Yadav |
| 2012/0172648 A1 | 7/2012 | Seebauer |
| 2012/0181163 A1 | 7/2012 | Inagaki et al. |
| 2012/0209090 A1 | 8/2012 | Goodall et al. |
| 2012/0235094 A1 | 9/2012 | Zhu et al. |
| 2012/0265122 A1 | 10/2012 | El-Shall et al. |
| 2012/0281428 A1 | 11/2012 | Davis et al. |
| 2012/0299175 A1 | 11/2012 | Tran |
| 2012/0329657 A1 | 12/2012 | Eastman et al. |
| 2013/0001067 A1 | 1/2013 | Boyd |
| 2013/0004778 A1 | 1/2013 | Tucker, III et al. |
| 2013/0015076 A1 | 1/2013 | Yoshida et al. |
| 2013/0032470 A1 | 2/2013 | Mohapatra et al. |
| 2013/0059396 A1 | 3/2013 | LeBoeuf et al. |
| 2013/0079577 A1 | 3/2013 | Ingram et al. |
| 2013/0099196 A1 | 4/2013 | Wu et al. |
| 2013/0102458 A1 | 4/2013 | Wong et al. |
| 2013/0150809 A1 | 6/2013 | Whiteford et al. |
| 2013/0156905 A1 | 6/2013 | Bourke, Jr. et al. |
| 2013/0163310 A1 | 6/2013 | Tran |
| 2013/0171060 A1 | 7/2013 | Vo-Dinh et al. |
| 2013/0180862 A1 | 7/2013 | Yoshida et al. |
| 2013/0184144 A1 | 7/2013 | Liang et al. |
| 2013/0189607 A1 | 7/2013 | Sakai et al. |
| 2013/0212789 A1 | 8/2013 | Conolly et al. |
| 2013/0216774 A1 | 8/2013 | Conolly et al. |
| 2013/0240758 A1 | 9/2013 | Bourke, Jr. et al. |
| 2013/0250403 A1 | 9/2013 | Maeda |
| 2013/0252798 A1 | 9/2013 | Ling et al. |
| 2014/0011013 A1 | 1/2014 | Jin et al. |
| 2014/0056947 A1 | 2/2014 | Adelung et al. |
| 2014/0069819 A1 | 3/2014 | Farrukh et al. |
| 2014/0093744 A1 | 4/2014 | Hu et al. |
| 2014/0106471 A1 | 4/2014 | Jeon et al. |
| 2014/0119026 A1 | 5/2014 | Davis et al. |
| 2014/0126269 A1 | 5/2014 | Tran |
| 2014/0134092 A1 | 5/2014 | Shankman |
| 2014/0147398 A1 | 5/2014 | Hamilton et al. |
| 2014/0160723 A1 | 6/2014 | Davis et al. |
| 2014/0163303 A1 | 6/2014 | Bourke, Jr. et al. |
| 2014/0174905 A1 | 6/2014 | Landry |
| 2014/0174906 A1 | 6/2014 | Landry |
| 2014/0213427 A1 | 7/2014 | Landry |
| 2014/0217330 A1 | 8/2014 | Worsley et al. |
| 2014/0220091 A1 | 8/2014 | Tofail et al. |
| 2014/0222117 A1 | 8/2014 | Bourke, Jr. et al. |
| 2014/0223997 A1 | 8/2014 | Gole |
| 2014/0225498 A1 | 8/2014 | Koo et al. |
| 2014/0227211 A1 | 8/2014 | Shankman |
| 2014/0242389 A1 | 8/2014 | Mahler |
| 2014/0243934 A1 | 8/2014 | Vo-Dinh et al. |

(56) References Cited

U.S. PATENT DOCUMENTS

| | | |
|---|---|---|
| 2014/0252275 A1 | 9/2014 | Landry et al. |
| 2014/0256534 A1 | 9/2014 | Gao et al. |
| 2014/0262743 A1 | 9/2014 | Landry et al. |
| 2014/0262806 A1 | 9/2014 | Jennings |
| 2014/0272030 A1 | 9/2014 | Bourke, Jr. et al. |
| 2014/0272623 A1 | 9/2014 | Jennings |
| 2014/0287237 A1 | 9/2014 | Mahler |
| 2014/0294721 A1 | 10/2014 | Feng et al. |
| 2014/0295102 A1 | 10/2014 | Di Carlo et al. |
| 2014/0301904 A1 | 10/2014 | Landry et al. |
| 2014/0301905 A1 | 10/2014 | Landry et al. |
| 2014/0311221 A1 | 10/2014 | Gole et al. |
| 2014/0323946 A1 | 10/2014 | Bourke, Jr. et al. |
| 2014/0326311 A1 | 11/2014 | Yang et al. |
| 2014/0336039 A1 | 11/2014 | Cohen et al. |
| 2014/0339072 A1 | 11/2014 | Jennings et al. |
| 2014/0342254 A1 | 11/2014 | Jennings et al. |
| 2014/0356574 A1 | 12/2014 | Conolly et al. |
| 2015/0036234 A1 | 2/2015 | Ben-Yakar et al. |
| 2015/0122639 A1 | 5/2015 | Liu et al. |
| 2015/0125829 A1 | 5/2015 | Hyman |

LOW TEMPERATURE, NANOSTRUCTURED CERAMIC COATINGS

CROSS REFERENCE TO RELATED APPLICATIONS

The present application is a Division of U.S. patent application Ser. No. 14/734,520, filed Jun. 9, 2015, now U.S. Pat. No. 10,828,400, issued Nov. 10, 2020, which is a non-provisional of, and claims priority under 35 U.S.C. § 119(e) to, U.S. Provisional Patent Application No. 62/010,003, filed Jun. 10, 2014, the entirety of which is expressly incorporated herein by reference.

STATEMENT OF GOVERNMENT RIGHTS

This invention was made with government support under NNX09AT30G awarded by NASA. The government has certain rights in this invention.

FIELD OF THE INVENTION

The present invention relates to the field of nano-ceramic coatings, and more particularly a process for depositing nanostructured ceramic coatings (e.g., low dimensional nanostructures such as nanoparticles, nanorods, nanoblades, etc.) on plastic substrates at low temperatures, and nano-ceramic coated plastic products and other substrates.

BACKGROUND OF THE INVENTION

Modifying material surfaces to enhance wear and corrosion resistance is a common practice for both military and commercial applications. Electrodeposited hard chrome is one of the most widely used protective coatings. Ceramic coatings, both single phase and composite types, are also common, and they are often applied using plasma spray. In this process, the coating material (usually in the form of a powder) is injected into a hot plasma stream, where it is heated and accelerated toward the substrate surface. After impacting the surface, the ceramic rapidly cools thus forming a coating layer.

Ceramic coatings have serious deficiencies that can limit their use. Plasma-sprayed ceramic coatings are somewhat less expensive than chrome (when clean-up costs are included), but are generally brittle and have limited success adhering to substrates, which is also a problem for hard chrome. The need for better coating materials has been recognized and considerable effort has recently gone into finding replacements.

Nanostructured materials are characterized by an ultra-fine microstructure with some physical aspect less than 100 nanometers in size. This feature can be grain size, particle or fiber/rod diameter, or layer thickness. There are two reasons why reducing the scale of a material's microstructure can significantly alter its properties. First, as grain size gets smaller, the proportion of atoms at grain boundaries or on surfaces increases rapidly. In a polycrystalline material with a grain size of 10 nm, as many as 50% of its atoms are at grain boundaries, resulting in a material with properties different significantly from the normal properties of the corresponding bulk (non-nanostructured) material. Second, many physical phenomena (such as dislocation generation, ferromagnetism, or quantum confinement effects) are governed by a characteristic length. As the physical scale of the material falls below this length, properties change radically.

Until recently, changes in deformation behavior and modes of failure as a result of nanostructuring of materials have not been well understood due to the inability to consistently fabricate high quality materials. This situation is changing rapidly, with considerable progress now being made in the fabrication of nanomaterials, as well as and the understanding of the interrelations between nanoscale processing, structure, and macroscale properties.

Plasma spray, one of the common processes used to fabricate ceramic coatings, is very simple in concept, but very complex in practice. An inert gas is passed through a region of electrical discharge, where it is heated to very high temperature (typically 10,000 to 20,000 K). The rapidly expanding plasma is forced out through a nozzle at velocities between 1,200 and 1,500 m/sec and directed toward a substrate. Particles are injected into the plasma, where they are heated and accelerated. Although the plasma and particle temperatures are high, and surface temperatures during the process are high, deep substrate heating is minimal. The complexity arises from the large number of parameters that must be selected and which can affect the structure and properties of the coating. The temperature and velocity of the plasma depend on the power applied to the gun, and the type and flow rate of the gas used. Usually, two gases are used, an inert gas such as helium or argon, and a secondary gas, such as hydrogen. Other factors include the morphology of the powder particles, distance from the gun to the substrate, position and orientation of the powder injection ports, and surface preparation of the substrate. Taken all together, these parameters determine the thermal history of the injected particles, velocity of impact, and flow and solidification characteristics after impact, thus dictating the resultant microstructure.

As compared to traditional plasma spray processes, plasma spraying of nanostructured materials introduces a number of complications. The first is that nanoparticles cannot be sprayed by particle injection into the plasma. Very small particles lack the momentum necessary to penetrate into the plasma, or to impact the surface while the plasma sweeps to the side near the substrate. To be sprayed, the particles must be formed into agglomerates approximately 30-100 microns in diameter. For an $Al_2O_3$—$TiO_2$ nanocomposite, this is usually accomplished by dispersing alumina and titania nanoparticles in a fluid with a binder and spray drying [1]. If necessary, the agglomerates are partially sintered to improve structural integrity.

The next problem is forming a nanostructured coating on the substrate. This is not trivial, since the agglomerates are greatly heated (promoting rapid grain growth) and are at least partially melted. There are three mechanisms for creating or retaining a nanoscale microstructure: avoiding melting or grain growth of the feedstock (very difficult), inclusion of nanoscale particles with very high melting temperature that remain solid while the rest of the material melts, or formation of a nanostructure during solidification of the sprayed material upon impact. The last mechanism occurs in composites consisting of two or more immiscible phases (as is the case for $Al_2O_3$ and $TiO_2$) and results from solid state decomposition of a single, metastable phase formed by rapid solidification during impact.

Therefore, while plasma spraying of nanostructured materials is known, there are significant limitations on the process, available compositions, and resulting coated product.

The obvious parameter by which to judge a "wear resistant coating" is wear rate. Wear can be termed as either sliding or abrasive. Both are measured by running a "wearing" medium over the surface and measuring weight loss. For many coatings, and particularly for brittle materials such as ceramics, this parameter can be misleading. The wear resistance of coatings in use today is outstanding, with wear rates orders of magnitude less than the uncoated surface.

Brittle coatings, however, usually do not fail by "wearing out", but rather suffer from cracking, delamination and spallation. At least as important with respect to the usefulness of a coating on a product as wear resistance are bond strength (adhesion to the substrate) and toughness (the ability to withstand an impact or applied strain). It is in these additional properties that the nanoceramic coatings excel to a remarkable degree.

The bond strength of the nanostructured coatings (e.g., tensile pull strength), is about double that of a conventional coating. S. Sengupta and A. Kumar, "Nano-Ceramic Coatings-A Means of Enhancing Bit Life and Reducing Drill String Trips Normal access", IPTC 2013: International Petroleum Technology Conference, Asset Integrity I (Mar. 26, 2013), earthdoc.eage.org/publication/publicationdetails/?publication=69795, expressly incorporated herein by reference. The toughness of the nanostructured $Al_2O_3$—$TiO_2$ coatings is extraordinary. Conventional (non-nanostructured) ceramic coatings show cracking and spalling. The nanostructured coating deforms along with the substrate and no macroscopic cracking is observed. A blow from a hammer severe enough to deform a steel substrate would not be sufficient to cause failure in the coating. This toughness translates into greater wear resistance, which is two to four times greater than that of the conventional coating. L. Kabacoff, "Nanoceramic Coatings Exhibit Much Higher Toughness and wear Resistance than Conventional Coatings", AMPTIAC Quarterly V. 6, No. 1, U.S. DOD DTIC Spring 2002, pp. 37-42, ammtiac.alionscience.com/pdf/AMPQ6_1ART05.pdf, expressly incorporated herein by reference.

SUMMARY OF THE INVENTION

Plastic products are now rapidly replacing a myriad of cookware items traditionally used by glasses and ceramics due to their durability, safety, and low manufacturing cost. Despite this trend, some people still prefer using expensive and more fragile ceramic/glass ware because the plastics can deteriorate over time after exposure to foods, which generate malodor, bad appearance, or color change.

Nano-Ceramic Coatings can be used to prevent these drawbacks while still retaining the advantages of the plastic products, as the coating only alters the surface of the plastics and not their bulk properties. The surface coating, however, adds functionality to the plastics, such as a self-cleaning property and disinfectant capabilities that result from a photocatalytic effect of certain ceramic systems. These ceramic coatings can also provide non-stick surface and higher temperature capabilities for the base plastics without using ceramic or glass materials.

Titanium oxide ($TiO_2$) and zinc oxide (ZnO) are good candidates for a nano-ceramic coating to deposit on plastics or plastic films used in the cookware and kitchenware. Both are a wide band gap semiconductor (3.0-3.2 eV for $TiO_2$ and 3.2-3.3 eV for ZnO), so they exhibit a photocatalytic property under UV light. This will lead to decomposition of organic compounds proximate to the coating, on exposure to sunlight or fluorescent lighting.

Water can be decomposed, using UV light, into oxygen and hydrogen, without the application of an external voltage, according to the following scheme:

$$TiO_2 \text{ or } ZnO + h\nu \rightarrow e^- + h^+$$

$$2h^+ + 2H_2O \rightarrow 2H^+ + 2 \cdot OH \rightarrow 2H^+ + H_2O_2$$

$$e^- + O_2 \rightarrow \cdot O_2^-$$

$$2 \cdot O_2^- + 4HO \cdot + H^+ \rightarrow 2H_2O_2 + 2O_2 + H_2$$

$$H_2O_2 \rightarrow 2HO \cdot$$

Ultimately, the hydroxyl radicals ($\cdot OH$) are generated in both the reactions. These hydroxyl radicals are very oxidative in nature and nonselective with redox potential of ($E_0$=+3.06 V). The hydroxyl radicals react with organic compounds to oxidize them, and often produce decomposition products. Oxidized and decomposed products tend to become more hydrophilic, and therefore can be more easily washed off by water, so the need for detergents may be reduced. See, Biplab Kumar Roy, Guangneng Zhang, and Junghyun Cho, "Titanium Oxide Nanoparticles Precipitated from Low-Temperature, Aqueous Solutions: III. Thin Film Properties", J. Am. Ceram. Soc., 95 [2] 676-683 (2012). The hydrogen peroxide is toxic to microorganisms. A highly crystalline film with a large surface area for the reaction is important for good photocatalytic (photovoltaic) performance of these oxides.

Low-temperature processing (<100° C.) is important to generating these ceramic coatings on plastic (polymeric) substrates, and especially thermoplastics, without destroying or modifying the underlying substrate.

One way of processing nano-ceramic coatings at low temperatures (<90-100° C.) is to take advantage of in-situ precipitated nanoparticles and nanostructures grown from aqueous solution. Solution based deposition techniques (thermohydrolytic or electrochemical) can generate oxide thin films at very low temperature and low cost. Such solution deposition technique relies upon hydrolysis for converting soluble metal salts into precipitates of metal oxides, and under controlled conditions, the precipitates are nanostructured. These nanostructures can tailor ceramic film formation and the subsequent microstructure development. In addition, aqueous solution deposition provides "environment-friendly" processing without toxic or flammable solvents. Low temperature processing has also shown versatility to generate various nanostructures. The growth of low-dimensional nanostructures (0-D, 1-D, 2-D) provides a means of enhancing the crystallinity of the solution-prepared films that is of importance for photocatalytic performance.

The present technology can generate durable, fully functional, and nano-ceramic coatings ($TiO_2$, ZnO) on plastic materials (silicone, Teflon, PET, PEN, acrylics, polyethylene, polypropylene, polycarbonate, PEEK, etc.) that possess both photocatalytic oxide properties and flexible plastic properties. Processing cost can be low, and does not require expensive equipment. Further, the process is scalable to permit implementation on a large scale. $TiO_2$ and ZnO are generally non-toxic, and therefore may be used in food environments.

According to one embodiment, ZnO film deposition is preferred due to the strong crystalline nature of the film deposited, as compared to that of $TiO_2$ films under similar processing conditions. The forced-hydrolytic deposition of zinc oxide from different soluble salts (e.g., zinc acetate, zinc nitrate and zinc chloride) all produced highly crystalline structure. With a seed layer mediated, low-temperature hydrothermal and electrochemical method (<90° C.), vertically aligned ZnO nanorods were grown. These highly crystalline nanorods dramatically increase surface area within the film, thereby enhancing the photovoltaic efficiency of the device.

The present technology therefore provides a low temperature process for laying down a thin layer of nanostructured ceramic onto surfaces, compatible with plastic products, such as kitchenware, including spatulas, bowls, containers, plastic flatware, serving dishes, wrapping films and even products that are used in hot environments such as in the oven or on a grill (providing the substrate, e.g., plastic, is already capable of withstanding those temperatures). The coating further typically has the property of keeping the plastic from absorbing odors or stains, and would not generally interfere with the plastic's other bulk properties, such as flexibility and light weight. It will also help keep the item's shape, which can deform over repeated use. The coating can, if desired, increase the durability of the item being coated and extend its useful life. It can also be provided to add stiffness to an item, if desired, and some ceramic feel, when held.

The type of substrate is non-critical, and in particular an aspect of the present technology permits coating of temperature-sensitive substrates with a photocatalytic ceramic layer, which may also have advantageous mechanical and chemical properties. The configuration of the substrate is also non-critical, and in particular, the process is not limited to coating of planar surfaces. The surface should be hydrophilic, which is typically achieved by having a preponderance of hydroxyl moieties on the surface. In some cases, a substrate is formed of a clean hydrophilic material, and no modification is required. In other cases, the surface may need to be cleaned, and a cleaning solution such as piranha ($H_2O_2/H_2SO_4$) or base piranha ($H_2O_2/NH_4OH$) is often suitable, since this cleans and hydroxylates. In some cases, a strong acid or base is sufficient to clean an otherwise hydrophilic surface. Often, an oxygen plasma treatment after cleaning is also useful to ensure the hydrophilicity of the surface.

The substrate surface may be dense or porous. A smooth non-porous surface is useful to form traditional ceramic film coatings, though in some cases a seed layer is provided to help form a high quality film with controlled crystallinity and tailored microstructures. Such films may provide both photocatalytic properties and mechanical/chemical properties.

A porous or otherwise high surface area surface, such as wood, natural fibers, foams, woven or non-woven fabrics may also be coated or in some cases, impregnated with the nano-structured ceramic particles or nanorods. In this case, it is typically the photocatalytic properties which are predominant.

The coating process typically proceeds either with the formation of nanoparticles in solution near the surface of the substrate to be coated, with an agglomeration of particles and densification of the particles at the surface, or with the nucleation and growth of nanostructures at the surface of the substrate to be coated. This process is typically driven by a supersaturation of a solution. Three methods are available. First, immersion in a supersaturated solution leads to surface deposition. Second, a solution may be sprayed onto a surface, in either a fully controlled environment (to control, e.g., temperature, headspace gas composition and thus solution pH, etc.), or in air, with deposition occurring by precipitation of nanoparticles in the droplets, and the mechanical force of the spray. Third, an electrochemical reaction may be provided to locally increase the precipitation conditions for ceramic particles at or near the surface to be coated.

Each of these embodiments, according to the present technology, can be conducted with maximum process temperatures below 100-130° C., and in particular, can generally be conducted at 90° C. or below. In some cases, temperatures at 60° C. or below are employed. Further, some embodiments employ mild reagents that permit use of reactive or fragile substrates.

A range of natural and synthetic polymers, and blends/composites may be employed. Natural materials that may be coated include wood (and wood composite materials), paper, cardboard, bamboo, fibers such as cotton, linen, wool, silk, leather, hemp, and jute, and polymers such as rubber, gutta-percha, and shellac. Many of these materials are microporous, and inherently hydrophilic, though various treatments during manufacture may render then less hydrophilic or hydrophobic, and therefore an initial cleaning and treatment may be required to increase hydroxylation of the surface. A coating on these types of materials will tend to be integrated in the surface region, and only after the pores and crevices are filled, will a more continuous coating form. The filling of the pores and crevices will tend to alter the mechanical properties and feel of the material. In some cases, the photocatalytic coating will tend to degrade the substrate material over time; however, lignin-based materials may have an ability to persist under oxidizing conditions for some time.

Synthetic fiber materials, which may be woven or non-woven, include polyester, acetate, acrylic (acrylonitrile), viscose, cellulose acetate, olefin, aramids (e.g., Kevlar), polybenzimidazole, orlon, vectran, polylactic acid, nylon, lastex (latex), rayon, spandex, viscose, polypropylene, fiberglass, carbon, polyvinyl chloride, polytetrafluoroethylene (PTFE), polyethylene (ultra-high molecular weight, high molecular weight, high density, medium density, low density, ultra-low density), urea-formaldehyde, and various reconstituted cellulose fibers. In general, these tend to have lower fiber porosity than natural fibers, and generally require an initial treatment to increase hydrophilicity. Note that, in some cases, the fiber may be manufactured with a hydrophilic copolymer or block copolymer that provides inherent hydrophilicity. Otherwise, a post treatment, such as piranha cleaning and oxygen plasma treatment, may be used to establish a hydrophilic surface. As with natural materials and fabrics, the synthetic fibers do not provide a flat surface or expanse for deposition of a coating, and therefore the precipitated nanoparticles or nanorods will tend to fill porosity and crevices before forming a more continuous coating outside the material.

In the case of high quality, elongated zinc oxide nanorods, the deposition on a fabric or surface with a conductive base can result in a piezoelectric generator, which produces a current based on movement. See, e.g., Azam Khan, Mazhar Ali Abbasi, Mushtaque Hussain, Zafar Hussain Ibupoto, Jonas Wissting, Omer Nur and Magnus Willander, "Piezoelectric nanogenerator based on zinc oxide nanorods grown on textile cotton fabric"; Naveed Sheikh, Nitin Afzulpurkar, and Muhammad Waseem Ashraf, "Robust Nanogenerator Based on Vertically Aligned ZnO Nanorods Using Copper Substrate", Appl. Phys. Lett. 101, 193506 (2012); dx.doi.org/10.1063/1.4766921; Journal of Nanomaterials, Volume 2013 (2013), Article ID 861017, dx.doi.org/10.1155/2013/861017; Zhong Lin Wang and Jinhui Song, "Piezoelectric Nanogenerators Based on Zinc Oxide Nanowire Arrays", Science v. 312 pp. 242-246 (2006), each of which is expressly incorporated herein by reference.

More generally, the substrate material may be Polyester (PES); Polyethylene terephthalate (PET); Polyethylene (PE); High-density polyethylene (HDPE); Polyvinyl chloride (PVC); Polyvinylidene chloride (PVDC); Polyvinylidene fluoride (PVDF) Low-density polyethylene (LDPE); Polypropylene (PP); Polystyrene (PS); High impact polystyrene (HIPS); Polyamides (PA) (Nylons); Acrylonitrile butadiene styrene (ABS); Polyethylene/Acrylonitrile Butadiene Styrene (PE/ABS); Polycarbonate (PC); Polycarbonate/Acrylonitrile Butadiene Styrene (PC/ABS); Polyurethanes (PU); Maleimide/Bismaleimide; Melamine formaldehyde (MF); Plastarch material; Phenolics (PF); Polyepoxide (Epoxy); Polyetheretherketone (PEEK); Polyetherimide (PEI); Polyimide; Polylactic acid (PLA); Polymethyl methacrylate (PMMA); Polytetrafluoroethylene (PTFE); Urea-formaldehyde (UF); Furan; Silicone; and Polysulfone.

According to some embodiments, the coated product is disposable (i.e., made for one time or seasonal use), and in such form may comprise a biodegradable or environmentally degradable polymer. According to one embodiment, the photocatalytic coating is capable of rapidly degrading the substrate, such that after the single or limited use, the substrate rapidly degrades under ultraviolet (UV) illumination or natural sunlight. According to other embodiments, the coated product is designed to be durable, and may be fabricated using a substrate material such as glass, ceramic, wood or metal. Typically, short duration use plasticware is made from different (and less costly) materials than long term use plasticware; further, products intended to be disposable tend to be photodegradable or biodegradable, while durable products typically avoid spontaneous degradation materials. The coating may be deposited directly on the plastic substrate, or deposited on an intermediate layer, such as a metallic or conductive film. See, U.S. Pat. Nos. 8,621,755, 8,176,641, 6,983,542, 5,280,052, 5,177,124, each of which is expressly incorporated herein by reference.

The present technology provides various benefits, resulting from the new form factors enabled. For example, photocatalytic drapes, curtains or blinds permit deodorizing a room using sunlight as a source. Medical devices, such as intravenous lines, catheters, and other transcutaneous devices may be coated to provide antibacterial properties based on the ultraviolet light emitted by fluorescent bulbs in a medical environment. More generally, all surfaces in a medical environment are subject to coating, including beds, headboards, siderails, etc., bed stands, medical equipment, trays, cups, pitchers, knives, forks, spoons, bedpans, trash receptacles, medical and surgical device packaging, and a full range of materials and configurations. The deposition process does not include any toxic products, and often does not unintentionally impair material properties.

Typically, the ceramic coating is a final or near-final manufacturing step, because the coating can be disrupted or cracked by various forces. As a result, in many cases, even relatively heat resistant substrates, which typically can withstand 100° C. as a bulk material, suffer deformation or degradation when in the form of a finished product.

Another product enabled by the present technology is photocatalytic water disinfection and treatment systems in third-world environments. For example, the coating may be applied to various clean, hydrophilic surfaces, and when properly applied, will produce hydroxyl radicals and hydrogen peroxide upon exposure to sunlight and moisture. Therefore, water troughs exposed to sunlight can disinfect the contents, and degrade dissolved organic compounds. The troughs can be coated in situ or near the place of use, and because the choice of materials is not narrowly constricted, a photocatalytic coating may be provided for existing installations, and in new installations, without displacing incumbent systems, suppliers, or maintenance systems. For example, a spray-applied coating driven by a steam generator to provide pressure and heat (to, e.g., 75-90° C. at the point of application) in a modestly controlled environment, using the zinc acetate technology discussed below, is used to coat plastic tubes or troughs through which contaminated water flows during daylight. (During night time or inclement weather as required to meet demand, UV light may be provided synthetically, or other source of disinfecting agent supplied).

The hydrogen peroxide and hydroxyl radical are somewhat toxic to organisms living in the water, and therefore the technology can also be exploited to reduce mosquito populations. In some areas of the globe where malaria and other insect borne diseases are endemic, standing water in old tires has been identified as a significant breeding ground for mosquitos. Therefore, if the inner wall of a tire is coated during manufacture with a photocatalytic coating, after it is removed from a vehicle, the coating should remain, and interact with sunlight to render the tire an inhospitable environment for mosquito larvae. Other configuration traps may be provided to lure female mosquitos into laying their eggs in a self-sterilizing environment.

A biocidal device is therefore provided, comprising at least one surface configured to retain natural rainwater and be exposed to sunlight, the at least one surface being coated with a nanostructured ceramic coating having a thickness in excess of 100 nm, formed by a deposition of at least one of titanium dioxide and zinc oxide nanostructures from a supersaturated aqueous ceramic precursor solution in a deposition process which does not require the at least one surface to be heated above 100° C., wherein the biocidal device produces larvicidal reaction products of rainwater when exposed to the sunlight.

Another environment for application of the technology is bathrooms. For example, toilet seats, counters, cabinets, floors, walls, tiles, sinks, faucets, hardware, etc., may be provided with a photocatalytic coating. Advantageously, when the regular light is turned off, a UV light source (gas discharge, fluorescent, LED, etc.) may be illuminated to drive the photocatalytic process. Personal articles, such as toothbrushes, combs, hair brushes, etc., can also be coated. In some cases, in the case of personal articles, a cabinet or case may be provided which provides a source of UV light when the object is not in use. Similarly, a dish washer may include an internal UV light source, to activate the photocatalytic effect for coated items contained inside. Indeed, the entire inside of the dish washer (or other enclosed space) may be coated with the photocatalytic coating, since this will generally increase the levels of hydroxyl radicals in the washwater, which in turn will facilitate cleaning of the contents.

The technology may also be used to coat portions of a car or other vehicle. The coating is provided, for example, on the exterior or interior surface(s), and the photocatalytic property is exploited to facilitate self-cleaning.

Similarly, in a clothes washer, the various surfaces, such as the drum (outer surface) and inner wall of the wash chamber provide high surface areas that may be coated with a photocatalytic material, and in use may be exposed to ultraviolet light. These surfaces are often metal or enamel coated, and not intrinsically heat sensitive; however, as the washing machine is fabricated, various heart sensitive elements are added. Therefore, while these surfaces are not plastic, they may benefit from the present technology. In use, the wash water is enriched in hydroxyl radicals as a result of the photocatalysis, resulting in reduced need for detergent and bleach, and reduced odor and possible bacterial or fungal contamination.

In other embodiments, the articles to be coated are in the kitchen or dining environment. Some of these coated plastic products according to the present technology are designed to react with organic compositions from food resulting in stains, odor absorption, or discoloration of the plasticware. Therefore, under exposure to ultraviolet light or sunlight, the organic compositions are oxidized and degraded, which can directly bleach many stains, and otherwise solubilize organic debris. In some environments, UV light is not naturally present. Therefore, according to one embodiment, a UV light source is provided within a cleaning environment, such as a dish washer, conveyor washer, plastic bus tub, dish rack, table or counter. The UV light source may be, for example, a gas discharge lamp or light emitting diode. In a kitchen, the areas that may be coated include utensils, plumbing fixtures, counters, walls, floors, tables, appliances, etc. For example, in a refrigerator or freezer, an ultraviolet lamp may illuminate photocatalytic coated surfaces, resulting in odor reduction, antibacterial effect (both direct from UV exposure, and indirect from hydrogen peroxide and hydroxyl radicals). In some cases, for example the refrigerator, a control system is provided to induce the photocatalytic effect when needed, and save energy and avoid possible side effects of UV light when not required. Assuming odor control is a goal, an odor sensor, such as a semiconductor sensor (possible in the form of a thermistor) or voltammetric sensor, is provided. Other odor sensors include MEMS/nanocatilever sensors, IS-FETs, and enzymatic sensors, and the like. In any case, the UV lamp, and in some cases, a source of moisture, are activated when odors are detected. The system can be a closed loop control system, or triggered periodically for a fixed cycle, i.e., after triggered, the process follows a predetermined course, such as 1 hour of UV and moisture, regardless of the trigger level and the measured effect of the process.

A photocatalytic water treatment system is therefore provided, comprising at least one surface configured to be wet with water and to be exposed to ultraviolet light, the surface being coated with a nanostructured ceramic coating having a thickness in excess of 100 nm, formed by a deposition of at least one of titanium dioxide and zinc oxide nanostructures from a supersaturated aqueous ceramic precursor solution in a deposition process which does not require the at least one surface to be heated above 100° C.; and an illumination system configured to illuminate the surface with ultraviolet light of sufficient intensity to treat water in the water flow path.

The surface may be an exposed wetted surface of a clothes washer isolated from contact with clothes, the illumination system further comprising a source of UV light configured to supply UV light during operation of the clothes washer to the exposed wetted surface.

The surface may also be an interior surface of a refrigerator, the illumination system further comprising a source of UV light configured to supply UV light during operation of the refrigerator to the interior surface and a source of moisture to wet the interior surface. Advantageously an odor detection sensor may be provided, along with an automated control to control at least the UV light in dependence on an output of the sensor.

With time, normal plasticware can also warp and lose its shape, for example due to residual stresses from a manufacturing process (e.g., injection molding) and the exposure to heat and UV radiation. Further, the use of plastics in microwave ovens or with hot food causes concerns for some consumers who worry about toxic chemicals leaching out of the plastic, even when the plastic is BPA-free (Bisphelol A or BPA is an additive for plastic and is also used in some plastic coatings products that has been found to cause some harm in laboratory animals, though not specifically in humans). The coating may be engineered to maintain the surface condition and configuration of the plasticware, and thus avoid or reduce deformation over time, and/or leaching of materials out of the plasticware. Further, the nanostructured ceramic coating generally does not itself contain leachable organic components, and therefore provides a barrier.

The coating also has photocatalytic properties that can reduce dirt buildup (i.e., require less soap or detergent to clean) and make the coated products easy to disinfect under UV light. Plus, having a ceramic coating over plasticware can repel potential bacterial buildup that can degrade the plastic. Finally, while the coating is ceramic, it does will not chip or break off if an item coated with it, if it is dropped.

The coating may be transparent, opaque, or tinted, and preferably includes inorganic components that do not disrupt the photocatalytic effect of UV light on the ceramic nanostructures, and avoids organic components, especially those that would degrade when subject to hydroxyl radicals from photocatalysis, and organic or inorganic components that would defeat the photocatalytic process by, for example, quenching free radicals, filtering UV light, significantly competing for UV photon capture, or provide a secondary path for release of the activation energy of the UV photons absorbed by the ceramic.

In some cases, the coating forms part of a photovoltaic cell generator or piezoelectric generator; these implementations typically compete for the energy needed to drive a photocatalytic process, and therefore within a given region of an object, there various implementations are not provided together. However, different regions of the substrate may have different functions, and a single coating may provide a basis for different end results. Therefore, while a photocatalytic product is one type of preferred embodiment, it is by no means the only useful result of depositing a nanostructured ceramic coating on a substrate.

Other products which may be produced using the technology include hair straighteners, having ceramic-coated plastic heating plates; window coatings (Yanfeng Gao; et. al. "Nanoceramic $VO_2$ thermochromic smart glass: A review on progress in solution processing,"; Volume 1, Issue 2, March 2012, Nano Energy, www.sciencedirect.com/science/article/pii/S2211285511000255 (accessed Sep. 4, 2012), expressly incorporated herein by reference); polyvinyl siding for residential, utility, and commercial buildings; laboratory plasticware; and dishwasher inner surfaces (Carter, John David; et. al. "Rinse aid surface coating compositions for modifying dishware surfaces," Aug. 8, 2006, U.S. Pat. No. 7,087,662, expressly incorporated herein by reference). Further products which may benefit from the nanostructured ceramic coating include screen protectors and/or oleophobic (anti smudge) lenses or surfaces for smartphones, tablets and touchscreens, smartphone cases, keyboards, automated teller machine (ATM), and other electronic device user interfaces, as well as stainless steel appliances and other exposed surfaces on which fingerprints may be evident. Dyes can be included in the coating as a finish to give appliances any tint, while enjoying the wear resistant and anti-smudge advantages of the coating.

DETAILED DESCRIPTION OF THE PREFERRED EMBODIMENTS

Example 1

General procedures of precursor solution preparation and titania film deposition are discussed in G. Zhang, B. K. Roy, L. F. Allard, and J. Cho, "Titanium Oxide Nanoparticles Precipitated from Low-Temperature Aqueous Solutions: II. Thin-Film Formation and Microstructure Developments," J. Am. Ceram. Soc., 93 [7] 1909-15 (2010), expressly incorporated herein by reference.

A preferred method for coating a plastic item is as follows. The surface of the plastic, which may have a mold release composition or other residual coating on it, is first cleaned, for example with freshly prepared piranha cleaning solution, i.e., $H_2O_2$ and sulfuric acid. A typical mixture is 3:1 concentrated sulfuric acid to 30% hydrogen peroxide solution, though a range of 2:1 to 7:1 may be used. Cleaning is conducted for 1-10 minutes at an appropriate temperature below 100° C., e.g., 60-90° C., though care is exercised to avoid significantly degrading the substrate, and the cleaning is ceased as soon as the surface is uniformly wetted and clean. The substrate is then dried in dry nitrogen gas ($N_2$) blow, and treated with an $O_2$ plasma (Harrick Plasma, Ithaca, NY) for 15 min to render the surface hydrophilic.

A desired amount of hydrochloric acid (HCl, 36.5%-38%, J. T. Baker, Phillipsburg, NJ) was first dissolved in ice-cold DI water (Barnsted E-pure, resistivity 18-20 MΩ-cm) followed by slow injection of adequate amount of titanium chloride ($TiCl_4$, 99.99%, Alfa-Aesar, Ward Hill, MA) in a parafilm-covered glass bottle for supersaturation. The method for calculating supersaturation at the deposition temperature is addressed in G. Zhang, B. K. Roy, L. F. Allard, and J. Cho, "Titanium Oxide Nanoparticles Precipitated from Low-Temperature Aqueous Solutions: I. Nucleation, Growth, and Aggregation," J. Am. Ceram. Soc., 91 [2] 3875-82 (2008), expressly incorporated herein by reference. Once prepared, the solutions were kept refrigerated until utilized.

The substrates may be seeded, by coating with compatible nanocrystals, such as by spin coating (e.g., for flat surfaces) or dipping in a seeding solution.

The substrates are then placed in a beaker containing freshly prepared precursor solution. The beaker was placed in an oil-bath, preset at 60-90° C., to perform the deposition. The pH of the solution is maintained by addition of a suitable acid, such as HCl for $TiCl_4$ (pH <1.5).

The process is preferably conducted at temperatures below 90° C., both to avoid damage to the substrate, and because the low temperature maintains a slow reaction rate and higher quality smaller crystals. As temperature increases, the reaction rate increases, and larger crystals with higher crystallinity result.

The coating may be facilitated by an electrochemical process. The substrate is selected as one which is inherently conductive, or coated with a conductive surface, such as a metal. In this case, hydrogen peroxide is added to the precursor solution, for example, 10 mM hydrogen peroxide in 5 mM $TiCl_4$ in 3:1 methanol-DI water. For example, the substrate is held at a cathodic deposition potential, with current held at a level which does not result in apparent hydrogen generation (bubbling), which might reduce coating quality. For example, the cathode voltage is held between about −3V to −5V with respect to a platinum foil reference electrode (anode) in the solution. pH and voltage may be adjusted to control both hydrogen bubble formation and corrosion of the conductive substrate. See, Biplab K. Roy, Guangneng Zhang, Roy Magnuson, Mark Poliks, and Junghyun Cho, "Electrodeposition of Titania Thin Films on Metallic Surface for High-k Dielectric Applications", J. Am. Ceram. Soc., 93 [3] 774-781 (2010), expressly incorporated herein by reference.

The deposition is conducted to produce a coating of the desired thickness, and may be monitored by pH change (and amount of acid needed to titrate the solution to maintain pH), time and electrical current, etc., or by mechanical or functional measurements. The precursor solution is changed at every hour to increase the deposition rate and to avoid any heavy particle agglomeration.

The surface morphology and crystallinity of the resulting thin films can be controlled by changing solution parameters. A thermodynamic parameter, supersaturation (S), has been identified as a key controlling factor to tailor such variations.

After desired deposition periods, films were cleaned with ethanol and dried under mild $N_2$ blow.

Titania particles form electrochemical conversion of $TiCl_4$ to $TiO_2$ in the solution, via thermal-energy-driven homogeneous nucleation. The thin film formation occurs by attraction and assembly of nanoparticles on substrate surface. Precursor solution environment not only determines the nanoparticle assembly and the film microstructure, but also influences the phase of titania (amorphous, anatase, or rutile).

Films obtained from very low S (~3.9) solution typically have a distinct "leaf-like"-structured surface morphology, with traces of anisotropic structured growth extending from the substrate surface to the top edge of the film. Growth rates in low S precursor are higher than in high S precursor. With increasing supersaturation (i.e., S ~232.8), bulk precipitation becomes more dominant with less contribution toward film formation and hence, the film growth rate decreases. A low S solution contains more HCl and less $TiCl_4$. Increased HCl imparts a common ion (Cl−) effect and prevents dissociation of $TiCl_4$, and low supersaturation can therefore be achieved. In this process, high S solution inherently has higher pH, whereas low S solution shows lower pH. Three phases of titania (namely rutile, anatase, and amorphous) are formed.

At very high supersaturation, the rate of hydrolysis is much faster than condensation. This situation can lead to random polycondensation of hydrolyzed octahedra and generation of amorphous phase. Therefore, at higher supersaturations, anatase phase surrounded primarily with amorphous titania is obtained. Amorphous phase content increases with increase in supersaturation and leads to the formation of denser and smoother film morphology. In contrast, low S conditions primarily produced directed rutile-type crystalline growth and porous films with rough topology.

Although anatase and rutile crystals can be observed in the deposited films, the presence of amorphous phase cannot be ignored in overall film morphology. Due to rapid hydrolysis characteristics of $Ti^{4+}$, even in very controlled deposition conditions, polycrystalline films contain an amorphous phase along with nanocrystalline particles. Therefore, in all situations, it is important to realize the composite nature of the films with some dominating phases. From low S precursors, rutile phase appears as a dominant one. As the supersaturation increases, the anatase phase first dominates in the film structure and the amorphous phase becomes prevalent at even higher supersaturations. In low S deposited rutile-containing films, porosity and segmented structure of aligned plates limits is evident. The optical absorption spectrum of rutile films obtained from low S solution is markedly different from that of films obtained from higher supersaturations.

Highly acidic low-supersaturation solutions produce a rutile-type of crystallinity and porous morphology, whereas the higher supersaturation results in the formation of amorphous and anatase phase with a denser microstructure. UV-Vis studies reveal a distinct difference in the optical absorptions between films formed from low S and high S $TiCl_4$ precursor solutions. The rutile-based films displayed a lower optical band gap than the films containing anatase/amorphous phases. Due to their densely packed particulate structure, the films obtained from high S showed higher mechanical properties than the porous rutile films. Dielectric properties of the rutile films were, however, superior to the anatase/amorphous films because of significant difference in dielectric constants among amorphous, anatase, and rutile phases. This offers a way of tuning thin film dielectric properties by manipulating the phase evolution with controlled solution parameters. The photoelectrochemical response is higher for the rutile-containing films, attributable to higher porosity (leading to more dye absorption, higher interaction area), higher refractive index, better crystallinity, and larger thickness of the low S generated films compared to their high S counterparts.

Example 2

Zinc oxide (ZnO) films consisting of vertically aligned nanorods may be hydrothermally grown on a seed layer at e.g., 90° C. using two alternate precursors (zinc acetate, zinc nitrate). Vertically grown nanorods exhibit the (002) out-of-plane texture and their size, alignment, density, and growth rate can be controlled by both solution and seed layer conditions. A continuous or stepwise deposition may be implemented. A seed layer, e.g., $ZnAc_2$ may be deposited and cured at temperatures as low as 100° C. In-situ precipitated nanoparticles and nanostructures from aqueous solution are provided. See, Sunghee Lee, Biplab Kumar Roy, and Junghyun Cho, "Vertically Aligned ZnO Nanorods Grown by Low-Temperature Solution Processing", Japanese Journal of Applied Physics 52 (2013) 05DA09, expressly incorporated herein by reference.

Zinc oxide (ZnO) is a direct wide band gap (3.4 eV) semiconductor, which is comparable to $TiO_2$, while having several advantages over $TiO_2$ such as easy crystallization at low temperature, 1D anisotropic growth, and high electron mobility. A hydrothermal process to produce the film employs low process temperatures, which permit use of flexible polymer substrates. Compared to other solution-based techniques which utilize open bath, the hydrothermal processing provides high controllability of nanostructures because of the mild deposition condition resulting from the higher solubility of zinc ions than, for example, titanium ions. Vertically aligned nanorods or nanotubes have shown some advantages over the nanoparticle clustered structures for enhanced photovoltaic (PV) properties due to their faster electron transport and reduced charge recombination. A seed layer may be provided to assist in in aligning the nanorod structure on the substrate.

The surface of the plastic substrate, which may have a mold release composition or other residual coating on it, is first cleaned, for example with freshly prepared piranha cleaning solution, i.e., $H_2O_2$ and sulfuric acid. A typical mixture is 3:1 concentrated sulfuric acid to 30% hydrogen peroxide solution, though a range of 2:1 to 7:1 may be used. Cleaning is conducted for 1-10 minutes at appropriate temperature, though care is exercised to avoid significantly degrading the substrate, and the cleaning is ceased after the surface is uniformly wetted and clean. The substrate is then dried in dry nitrogen gas ($N_2$) blow, and treated with an $O_2$ plasma (Harrick Plasma, Ithaca, NY) for 15 min to render the surface hydrophilic.

The treated substrate can be coated with a thin layer of a 1:1 molar ratio of zinc acetate dihydrate and ethanolamine in 2-methoxyethanol (all three from Alfa Aesar), in a concentration range of e.g., 50 mM-750 mM, though other concentrations may be employed as appropriate. The solutions may be pre-heated at 60° C. for 40 min in a water bath before coating, and cured at less than 90-100° C.

On the seed layer, ZnO films may be grown by hydrothermal deposition. Two types of precursors may, for example, be used: i) 20 mM zinc acetate dihydrate and 20 mM hexamethylenetetramine (HMT; Alfa Aesar); ii) 25 mM zinc nitrate hexahydrate (Alfa Aesar) and 25 mM HMT aqueous solution. Seed layer coated substrate is immersed into the precursor solution. The deposition may be conducted at 60-90° C. The deposition may be, for example, 2-8 hours, and may be repeated to build up layer thickness and density. For example, 4 2-hour sessions may be conducted with a gentle wash and solution replacement between each deposition. During the hydrothermal deposition, bulk precipitates may form, in the precursor solution, and therefore the solution may be replaced with a freshly prepared solution every 1-2 h.

A hydrothermal spray coating process is also possible, in which particles are formed in a hot supersaturated solution and sprayed with force on an object, to provide a mechanical impact effect to facilitate agglomeration of particles at the surface of the substrate. The solution can be allowed to dry after spraying. In a spray coating embodiment, it is useful to maintain the substrate at elevated temperature, e.g., 60-90° C.

After the hydrothermal deposition, the ZnO films were rinsed with deionized water, and blow dried with nitrogen gas.

Synthetic oxide films in aqueous solution are formed under an accelerated hydrolysis environment for a relatively short period. Such hydrolysis process of precursor species strongly depends solution parameters such as pH, concentration and temperature. The solubility of the oxides and their hydroxides need not be known, and the thermodynamics data may be used to calculate equilibrium solubility for the stable phases, from which the degree of supersaturation S can be calculated. It provides the driving force for nucleation and growth of the oxide nanostructures. G. Zhang, B. K. Roy, L. F. Allard, and J. Cho: J. Am. Ceram. Soc. 91 (2008) 3875.

Depending on the availability of OH— (i.e., with pH of solution) the extent of hydrolysis may vary. In the Zn—OH system, soluble species of Zn (II) ions include $Zn^{2+}$, $Zn(OH)^+$, $Zn(OH)_2$, $Zn(OH)^{3-}$, and $Zn(OH)_4^{2-}$. A preliminary calculation indicated that S at pH 7 or lower is extremely small compared to that of Ti—OH, and therefore a complexing agent such as HMT ($C_6H_{12}N_4$) or dimethylamine borane [DMAB, $BH_3NH(CH_3)_2$] is provided to assist in precipitating a ZnO phase. Due to the complexing agent, $Zn^{2+}$ cation also forms amine complexes such as $Zn(NH_3)_4^{2+}$ with $NH_3$(aq) in moderately basic solution.

A higher degree of supersaturation S can be attained either by increasing temperature or by increasing pH of the solution, so subsequent precipitation can be accelerated.

The nanorods from a zinc acetate precursor solution tend to show straighter and more densely packed structure while those from a zinc nitrate precursor are less vertically aligned and less dense. The morphological difference between the films produced by different precursors is likely due to different pH values of the solutions. The initial pH values for the zinc acetate based precursor and the zinc nitrate based precursor are, for example 6.95 and 6.82, respectively. The difference in pH over 0.1 can in fact make a significant change in terms of the degree of supersaturation, which is the driving force for nucleation and growth of the ZnO nanorod. Therefore, high pH in the case of zinc acetate precursor will yield more nucleation density for ZnO rods and make them more packed and straight during the growth. The effects of ionic species generated from different precursors alters the stabilization of the rod surfaces (particularly, basal plane vs non-basal planes); by inactivating non-basal planes (m-planes) through ion attachment, the aspect ratio can increase and the rod growth can be faster.

Nanorod films may have a thickness range, for example, from 350 to 1700 nm, without cracks or film delamination.

Example 3

A polymeric substrate in the form of a molded, extruded, or formed useful article, subject to degradation by extended temperatures in excess of 100° C. is provided. The substrate is initially prepared to ensure a hydrophilic surface. For example, the article may be immersed or coated with piranha cleaning solution ($H_2O_2$ and sulfuric acid), for a sufficient time to fully clean the surface, but the process is limited to avoid substantial damage to the article. The substrate is then dried and may be treated with oxygen plasma to render the surface hydrophilic. In some cases, the surface may be masked, either to selectively produce hydrophilic properties, or to subsequently block the surface, to produce a latent pattern.

The substrate is, for example, formed from polyethylene terephthalate (PET), PEEK, polyurethane, nylon, epoxides, polyamides, polyaramides, polyvinyl chloride, polystyrene, ABS (acrylonitrile and styrene, toughened with polybutadiene), polyethylene, polypropylene, polycarbonate, Teflon® or other fluoropolymer, silicone, silicone heteropolymer or copolymer, etc. Rubbers and elastomers may also be treated. Films and panes, especially optically transmissive structures, may be employed as well.

The useful article is, for example, a kitchen utensil, an eating utensil (knife, fork, spoon), kitchenware (plate, bowl, cup), tray, table, headboard, cutting board, spatula, container, plastic flatware, serving dish, toothbrush, hair brush, or the like. The useful article can also be a disposable medical device, such as a catheter, intravenous line, suture, or other transcutaneous or patient-contact device, or simply an item provided in the patient room, recovery room, operating or procedure room.

The treated substrate may be pre-seeded per Example 2.

The substrate, which may be pre-seeded, is immersed in a supersaturated solution of ceramic precursor, and the supersaturated solution may be replenished after some period of deposition with an acid having the same counterions as the ceramic precursor cations, to maintain supersaturated deposition conditions. Process temperatures are maintained below a softening temperature of the molded useful article, i.e., below 100° C., and preferably below 90° C. throughout the process.

The deposition proceeds for 2-8 hours with the precursor solution replaced every 2 hours, to form a layer of ZnO nanorods e.g., 1,000 nm thick, and preferably in the range 250-3,000 nm thick.

Example 4

A low-density polyethylene mixed with polyisobutene (PIB) or poly[ethylene-vinylacetate] (EVA) copolymer 40-100 gage, biaxially oriented monolayer film is provided. One surface of the film is treated with an oxygen plasma to increase hydrophilicity. The hydrophilic surface is immersed in a supersaturated ceramic precursor solution, to selectively coat the hydrophilic surface with a nanostructured ceramic coating 100-350 nm thick. The resulting product is a ceramic-coated asymmetric cling wrap, with a sticky side and a ceramic coated side. The ceramic coating reduces permeability to oxygen and water, increases handleability, and provides photocatalytic properties. The process conditions are maintained below 100° C. Because of the tight radii that such a film may be subjected to, it is likely that the ceramic coating will suffer cracks if used as a traditional cling wrap. However, portions of the film that are not bent or crushed, should display a high ratio of photocatalytic activity to weight, and may be used to provide a temporary photocatalytic surface.

Example 5

A wood product, such as a cutting board, is provided. The wood is treated to ensure hydrophilicity, such as by acid or base, short piranha treatment, enzymatic treatment, or the like, and optionally an oxygen plasma treatment.

The wood is kiln dried at 100° C. and surface of the wood is saturated with 1:1 zinc acetate: and ethanolamine in 2-methoxyethanol, and then dried at 100° C. to leave crystal seeds.

The wood product is then immersed in a supersaturated solution of aqueous 20 mM zinc acetate/20 mM hexamethylenetetramine for two hours or more. The resulting product has a surface which is impregnated and coated with ZnO ceramic nanorods. It is noted that under ultraviolet illumination, with moisture, hydroxyl radicals and hydrogen peroxide are generated, which will tend to degrade the wood, but also degrade odors, food residue, and bacteria. The lignin in the wood is relatively resistant to oxidation, and therefore the reduction in product life is acceptable.

Example 6

A woven or non-woven fabric, such as a natural fiber, such as cotton, or linen, or a synthetic fiber such as polyester, nylon, rayon, PET, polyethylene, or the like is provided.

Depending on the fiber type, the substrate is treated to ensure a high degree of hydroxylation, such as by an acid treatment and/or oxygen plasma treatment. Hydrophobic substrates formed of non-porous fibers, such as ultra high molecular weight polyethylene, may be treated with piranha.

The hydrophilic substrate is saturated with 1:1 zinc acetate: and ethanolamine in 2-methoxyethanol, and then dried at 100° C. to leave crystal seeds. The seeded substrate is then immersed in a supersaturated solution of aqueous 20 mM zinc acetate/20 mM hexamethylenetetramine for two to eight hours. The resulting product has a surface which is impregnated with ZnO ceramic nanoparticles.

The fabric may, prior to coating, be formed into a useful article such as drapes or other window treatments. Under ultraviolet illumination, in the presence of moisture, hydroxyl radicals and hydrogen peroxide are generated, which will render the drapes hung in a window or as a room divider in hospital room settings as an air cleaner, to reduce odor tend to reduce bacterial growth and aerosol transfer.

Example 7

Metallized plastic silverware or a metallized plastic cell phone case is provided. See, U.S. Pat. Nos. 8,621,755, 8,176,641, 6,983,542, 5,280,052, 5,177,124. The substrate is prepared by treatment with oxygen plasma to render the surface hydrophilic.

A coating is formed by an electrochemical deposition process. The ceramic precursor solution includes 10 mM hydrogen peroxide in 5 mM $TiCl_4$ in 3:1 methanol-DI water. The substrate is held at a cathodic deposition potential, and maintained at a pH and voltage potential to avoid corrosion of the metallized coating and also avoid hydrogen bubbling, while driving formation of a ceramic coating.

A coating is formed as a single layer or in a series of layers, for example 30 seconds applied potential, 30 seconds altered potential (preferably, a cathodic protection potential for the metalized film) for 4 cycles, to form a ceramic layer of 250-1,000 nm.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims.

All patents and publications mentioned in this specification are expressly incorporated herein by reference in their entirety, and may be pertinent to various issues.

REFERENCES

1 J. T. Yates Jr, "Photochemistry on TiO2: Mechanisms Behind the Surface Chemistry," Surf. Sci., 603 [10-12] 1605-12 (2009).
2 Y. Xu, X. Zhu, Y. Dan, J. H. Moon, V. W. Chen, A. T. Johnson, J. W. Perry, and S. Yang, "Electrodeposition of Three-Dimensional Titania Photonic Crystals from Holographically Patterned Microporous Polymer Templates," Chem. Mater., 20 [5] 1816-23 (2008).
3 S. L. Kuai, X. F. Hu, and V.-V. Truong, "Synthesis of Thin Film Titania Photonic Crystals Through a dip-Infiltrating Sol-Gel Process," J. Cryst. Growth, 259 [4] 404-10 (2003).
4 S. Lazarouk, Z. Xie, V. Chigrinov, and H. S. Kwok, "Anodic Nanoporous Titania for Electro-Optical Devices," Jpn. J. Appl. Phys., 46 [7A] 4390-4 (2007).
5 B. H. Park, L. S. Li, B. J. Gibbons, J. Y. Huang, and Q. X. Jia, "Photovoltaic Response and Dielectric Properties of Epitaxial Anatase-TiO2 Films Grown on Conductive La0.5Sr0.5CoO3 Electrodes," Appl. Phys. Lett., 79 [17] 2797-9 (2001).
6 L. Zhou, R. C. Hoffmann, Z. Zhao, J. Bill, and F. Aldinger, "Chemical Bath Deposition of Thin TiO2-Anatase Films for Dielectric Applications," Thin Solid Films, 516 [21] 7661-6 (2008).
7 N.-G. Park, J. van de Lagemaat, and A. J. Frank, "Comparison of Dye-Sensitized Rutile- and Anatase-Based TiO2 Solar Cells," J. Phys. Chem. B, 104 [38] 8989-94 (2000).
8 M. R. Hoffmann, S. T. Matrin, W. Choi, and D. W. Bahnemann, "Environmental Applications of Semiconductor Photocatalysis," Chem. Rev., 95 [1] 69-96 (1995).
9 J. Y. Kim, D.-W. Kim, H. S. Jung, and K. S. Hong, "Influence of Anatase-Rutile Phase Transformation on Dielectric Properties of Sol-Gel Derived TiO2 Thin Films," Jpn. J. Appl. Phys., 44 [8] 6148-51 (2005).
10 B. K. Roy, G. Zhang, M. Yoo, I.-T. Bae, and J. Cho, "Developments of Low-Temperature Solution Processing for Nanostructured Titania Dielectric Films," Sci. Adv. Mater., 2 [1] 90-101 (2010).
11 W. J. E. Beek, M. W. Martijn, and R. A. J. Janssen, "Metal Oxide Polymer Bulk Heterojunction Solar Cell"; pp. 388-9 in Organic Photovoltaics, Edited by C. Brabec, V. Dyakonov, and U. Schref, Wiley-VCH, Weinheim, Germany, 2008.
12 V. G. Bessergenev, I. V. Khmelinskii, R. J. F. Pereira, V. V. Krisuk, A. E. Turgambaeva, and I. K. Igumenov, "Preparation of TiO2 Films by CVD Method and its Electrical, Structural and Optical Properties," Vacuum, 64 [3-4] 275-9 (2002).
13 H. W. Lehmann and K. Frick, "Optimizing Deposition Parameters of Electron Beam Evaporated TiO(2) Films," Appl. Opt., 27 [23] 4920-4 (1988).
14 B. K. Roy, G. Zhang, R. Magnuson, M. Poliks, and J. Cho, "Electrodeposition of Titania Thin Films on Metallic Surface for High-k Dielectric Applications," J. Am. Ceram. Soc., 93 [3] 774-81 (2010).
15 C. D. Lokhande, S.-K. Min, K.-D. Jung, and O.-S. Joo, "Cathodic Electrodeposition of Amorphous Titanium Oxide Films from an Alkaline Solution Bath," J. Mater. Sci., 39 [21] 6607-10 (2004).
16 B. K. Roy, Electrodeposition of Titania and Barium Titanate Thin Films for High-k Dielectric Applications, Ph.D. Dissertation, State University of New York, Binghamton, NY, 2010.
17 G. Zhang, B. K. Roy, L. F. Allard, and J. Cho, "Titanium Oxide Nanoparticles Precipitated from Low-Temperature Aqueous Solutions: I. Nucleation, Growth, and Aggregation," J. Am. Ceram. Soc., 91 [2] 3875-82 (2008).
18 G. Zhang, B. K. Roy, L. F. Allard, and J. Cho, "Titanium Oxide Nanoparticles Precipitated from Low-Temperature Aqueous Solutions: II. Thin-Film Formation and Microstructure Developments," J. Am. Ceram. Soc., 93 [7] 1909-15 (2010).
19 M. Henry, J. P. Jolivet, and J. Livage, "Aqueous Chemistry of Metal Cations: Hydrolysis, Condensation and Complexation"; pp. 153-206 in Structure and Bonding, Vol. 77, Edited by R. Reisfeld and C. K. Jorgensen, Springer-Verlag, Berlin, Germany, 1992.
20 F. P. Rotzinger and M. Graetzel, "Characterization of the Perhydroxytitanyl(2+) Ion in Acidic Aqueous Solution. Products and Kinetics of its Decomposition," Inorg. Chem., 26 [22] 3704-8 (1987).
21 M. Birkholz, P. F. Fewster, and C. Genzel, Thin Film Analysis by X-ray Scattering. pp. 148-55, Wiley-VCH, Weinhiem, Germany, 2006.
22 J. I. Pankove, Optical Processes in Semiconductors. pp. 35-42, Dover, NY, 1975.

23 S. D. Mo and W. Y. Ching, "Electronic and Optical Properties of Three Phases of Titanium Dioxide: Rutile, Anatase, and Brookite," Phys. Rev. B, 51 [19] 13023-32 (1995).

24 D. Reyes-Coronado, G. Rodrguez-Gattorno, M. E. Espinosa-Pesqueira, C. Cab, R. de Coss, and G. Oskam, "Phase-Pure TiO2 Nanoparticles: Anatase, Brookite and Rutile," Nanotechnology, 19 [14] 145605,10 pp (2008).

25 C. Yang, H. Fan, Y. Xi, J. Chen, and Z. Li, "Effects of Depositing Temperatures on Structure and Optical Properties of TiO2 Film Deposited by Ion Beam Assisted Electron Beam Evaporation," Appl. Surf. Sci., 254 [9] 2685-9 (2008).

26 A. Nakaruk, D. Ragazzon, and C. C. Sorrell, "Anatase-Rutile Transformation Through High-Temperature Annealing of Titania Films Produced by Ultrasonic Spray Pyrolysis," Thin Solid Films, 518 [14] 3735-42 (2010).

27 S. H. Kang, M.-S. Kang, H.-S. Kim, J.-Y. Kim, Y.-H. Chung, W. H. Smyrl, and Y.-E. Sung, "Columnar Rutile TiO2 Based Dye-Sensitized Solar Cells by Radio-Frequency Magnetron Sputtering," J. Power Sources, 184 [1] 331-5 (2008).

28 S. Burnside, J.-E. Moser, K. Brooks, and M. Graetzel, "Nanocrystalline Mesoporous Strontium Titanate as Photoelectrode Material for Photosensitized Solar Devices: Increasing Photovoltage Through Flatband Potential Engineering," J. Phys. Chem. B, 103 [43] 9328-33 (1999).

29 J. M. Bolts and M. S. Wrighton, "Correlation of Photocurrent-Voltage Curves with Flat-Band Potential for Stable Photoelectrodes for the Photoelectrolysis of Water," J. Phys. Chem., 80 [24] 2641-5 (1976).

30 R. Saha and W. D. Nix, "Effects of the Substrate on the Determination of Thin Film Mechanical Properties by Nanoindentation.," Acta Mater., 50 [1] 23-38 (2002).

31 W. C. Oliver and G. M. Pharr, "Improved Technique for Determining Hardness and Elastic Modulus Using Load and Displacement Sensing Indentation Experiments," J. Mater. Res., 7 [6] 1564-83 (1992).

32 R. B. King, "Elastic Analysis of Some Punch Problems for a Layered Medium," Int. J. Solids Structures, 23 [12] 1657-64 (1987).

33 M. J. Mayo, R. W. Sieigel, A. Narayanasamy, and W. D. Nix, "Mechanical Properties of Nanophase TiO2 as Determined by Nanoindentation," J. Mater. Res., 5 [5] 1073-82 (1990).

34 O. Zywitzki, T. Modes, H. Sahm, P. Frach, K. Goedicke, and D. Glo̅ ß, "Structure and Properties of Crystalline Titanium Oxide Layers Deposited by Reactive Pulse Magnetron Sputtering," Surf. Coat. Technol., 180-181 [1] 538-43 (2004).

35 P. Kern, P. Schwaller, and J. Michler, "Electrolytic Deposition of Titania Films as Interference Coatings on Biomedical Implants: Microstructure, Chemistry and Nano-Mechanical Properties," Thin Solid Films, 494 [1-2] 279-86 (2006).

36 Z. Burghard, L. P. Bauermann, A. Tucic, L. P. Jeurgens, V. Srot, P. Bellina, P. Lipowsky, R. C. Hoffmann, E. Gutmanas, J. Bill, and F. Aldinger, "Nacre-Like TiO2- and ZnO-Based Organic/Inorganic Hybrid Systems in 1007-S07-03," Mater. Res. Soc. Symp. Proc., 1007-S07-03 115-22 (2007).

37 Y. Gaillard, V. J. Rico, E. Jimenez-Pique, and A. R. Gonz'alez-Elipe, "Nanoindentation of TiO2 Thin Films with Different Microstructures," J. Phys. D: Appl. Phys., 42 [14] 145305, 9 pp (2009).

38 M. Agarwal, M. R. De Guire, and A. Heuer: J. Am. Ceram. Soc. 80 (1997) 2967.

39 B. C. Bunker, P. C. Rieke, B. J. Tarasevich, A. A. Campbell, G. E. Fryxell, G. L. Graff, L. Song, J. Liu, J. W. Virden, and G. L. McVay: Science 264 (1994) 48.

40 H. Cölfen and M. Antonietti: Angew. Chem. Int. Ed. 44 (2005) 5576.

41 G. Zhang, J. Y. Howe, D. W. Coffey, D. A. Blom, L. F. Allard, and J. Cho: Mater. Sci. Eng. C 26 (2006) 1344.

42 B. K. Roy, G. Zhang, and J. Cho: J. Am. Ceram. Soc. 95 (2012) 676.

43 B. K. Roy, G. Zhang, R. Magnuson, M. Poliks, and J. Cho: J. Am. Ceram. Soc. 93 (2010) 774.

44 B. K. Roy and J. Cho: J. Am. Chem. Soc. 95 (2012) 1189.

45 S. Yu, J. S. Lee, S. Nozaki, and J. Cho: Thin Solid Films 520 (2012) 1718.

46 M. Gräzel: J. Photochem. Photobiol. C 4 (2003) 145.

47 B. E. Sernelius, K.-F. Berggren, Z.-C. Jin, I. Hamberg, and C. G. Granqvist: Phys. Rev. B 37 (1988) 10244.

48 E. M. Kaidashev, M. Lorenz, H. von Wenckstern, A. Rahm, H.-C. Semmelhack, K.-H. Han, G. Benndorf, C. Bundesmann, H. Hochmuth, and M. Grundmann: Appl. Phys. Lett. 82 (2003) 3901.

49 R. Könenkamp, L. Dloczik, K. Ernst, and C. Olesch: Physica E 14 (2002) 219.

50 J. Wu and S. Liu: Adv. Mater. 14 (2002) 215.

51 A. Martinson, M. Goes, F. Fabregat-Santiago, J. Bisquert, M. Pellin, and J. Hupp: J. Phys. Chem. A 113 (2009) 4015.

52 L. Schmidt-Mende and J. MacManus-Driscoll: Mater. Today 10 [5] (2007) 40.

53 M. H. Huang, Y. Wu, H. Feick, N. Tran, E. Weber, and P. Yang: Adv. Mater. 13 (2001) 113.

54 J. H. Choi, H. Tabata, and T. Kawai: J. Cryst. Growth 226 (2001) 493.

55 J. X. Wang, C. M. L. Wu, W. S. Cheung, L. B. Luo, Z. B. He, G. D. Yuan, W. J. Zhang, C. S. Lee, and S. T. Lee: J. Phys. Chem. C 114 (2010) 13157.

56 X. Wang, Z. Tian, T. Yu, H. Tian, J. Zhang, S. Yuan, X. Zhang, Z. Li, and Z. Zou: Nanotechnology 21 (2010) 065703.

57 C.-H. Ku and J.-J. Wu: Nanotechnology 18 (2007) 505706.

58 K. Zhu, N. R. Neale, A. Miedaner, and A. J. Frank: Nano Lett. 7 (2007) 69.

59 S. Yamabi and H. Imai: J. Mater. Chem. 12 (2002) 3773.

60 L. E. Greene, M. Law, D. H. Tan, M. Montano, J. Goldberger, G. Somorjai, and P. Yang: Nano Lett. 5 (2005) 1231.

61 K. Govender, D. S. Boyle, P. B. Kenway, and P. O'Brien: J. Mater. Chem. 14 (2004) 2575.

62 C. Gumu, O. M. Ozkendir, H. Kavak, and Y. Ufuktepe: J. Optoelectron. Adv. Mater. 8 (2006) 299.

63 M. Suchea, S. Christoulakis, K. Moschovis, N. Katsarakis, and G. Kiriakidis: Thin Solid Films 515 (2006) 551.

64 M. R. Islam and J. Podder: Cryst. Res. Technol. 44 (2009) 286.

65 C. Y. Jiang, X. W. Sun, G. Q. Lo, D. L. Kwong, and J. X. Wang: Appl. Phys. Lett. 90 (2007) 263501.

66 A. D. Pasquier, H. Chen, and Y. Lu: Appl. Phys. Lett. 89 (2006) 253513.

67 J. Qiu, X. Li, W. He, S.-J. Park, H.-K. Kim, Y.-H. Hwang, J.-H. Lee, and Y.-D. Kim: Nanotechnology 20 (2009) 155603.

68 L. T. Kabakoff, "Nanoceramic Coatings Exhibit Much Higher Toughness and Wear Resistance Than Conventional Coatings"; AMPTIAC Quarterly Newsletter Spring 2002, vol. 6 No. 1.

69 Hoda S. Hafez, E. El-fadaly; "Synthesis, characterization and color performance of novel $Co^+$-doped alumina/ titania nanoceramic pigments," Volume 95, September 2012, *Spectrochimica Acta Part A: Molecular and Biomolecular Spectroscopy*, Sciencedirect web site, www.sciencedirect.com/science/article/pii/S1386142512004246 (accessed Aug. 4, 2012).
70 Su-Shia Lin; "Effect of substrate temperature on the properties of $TiO_2$ nanoceramic films," Volume 38, Issue 3, April 2012, *Ceramics International*, Sciencedirect web site, www.sciencedirect.com/science/article/pii/S0272884211009722 (accessed Sep. 4, 2012).
71 Su-Shia Lin, et. al. "$TiO_2$ nanoceramic films prepared by ion beam assisted evaporation for optical application," Volume 35, Issue 4, *Ceramics International*, Sciencedirect web site, www.sciencedirect.com/science/article/pii/S0272884208003015 (accessed September, 2012).
72 Yanfeng Gao; et. al. "Nanoceramic $VO_2$ thermochromic smart glass: A review on progress in solution processing,"; Volume 1, Issue 2, March 2012, *Nano Energy*, www.sciencedirect.com/science/article/pii/S2211285511000255 (accessed Sep. 4, 2012).
73 Carter, John David; et. al. "Rinse aid surface coating compositions for modifying dishware surfaces," Aug. 8, 2006, U.S. Pat. No. 7,087,662.

See also, U.S. Pat. Nos. 8,557,215, 8,492,319, 8,490,950, 8,476,206, 8,227,548, 8,227,072, 8,021,768, WO2011/061691, EP1835002, CN101190851, 6,350,397; 6,537,517; 6,764,796; 6,846,565; 6,918,946; 7,019,391; 7,071,139; 7,186,392; 7,229,600; 7,232,556; 7,285,188; 7,312,087; 7,330,369; 7,335,908; 7,354,850; 7,375,417; 7,393,699; 7,432,522; 7,476,607; 7,482,382; 7,489,537; 7,491,431; 7,498,005; 7,521,394; 7,524,370; 7,528,002; 7,541,509; 7,572,400; 7,575,784; 7,601,326; 7,601,327; 7,608,147; 7,630,227; 7,645,397; 7,655,274; 7,670,581; 7,677,198; 7,682,943; 7,687,431; 7,695,689; 7,713,955; 7,722,953; 7,745,813; 7,763,149; 7,826,336; 7,846,864; 7,864,560; 7,883,610; 7,901,660; 7,910,492; 7,911,035; 7,927,567; 7,931,683; 7,938,855; 7,942,926; 7,960,260; 7,973,997; 7,976,915; 7,977,402; 7,981,150; 7,988,947; 7,994,422; 8,002,823; 8,003,563; 8,029,554; 8,048,523; 8,049,203; 8,066,763; 8,067,054; 8,067,299; 8,067,402; 8,067,403; 8,070,797; 8,071,156; 8,076,846; 8,084,762; 8,089,681; 8,120,009; 8,163,084; 8,163,633; 8,178,122; 8,183,587; 8,187,620; 8,216,632; 8,221,655; 8,221,822; 8,227,817; 8,231,980; 8,242,481; 8,247,680; 8,268,381; 8,269,214; 8,277,631; 8,283,412; 8,287,937; 8,318,126; 8,318,297; 8,320,514; 8,323,982; 8,344,238; 8,353,949; 8,357,954; 8,376,013; 8,377,414; 8,389,958; 8,403,239; 8,415,556; 8,425,803; 8,426,817; 8,431,149; 8,432,604; 8,440,162; 8,449,603; 8,450,716; 8,450,717; 8,455,857; 8,541,337; 8,574,419; 8,574,615; 8,585,627; 8,592,037; 8,598,266; 8,609,205; 8,618,212; 8,618,509; 8,618,595; 8,624,105; 8,628,726; 8,629,076; 8,632,663; 8,647,292; 8,647,915; 8,652,409; 8,652,874; 8,653,497; 8,663,380; 8,664,143; 8,669,325; 8,679,580; 8,681,925; 8,702,640; 8,706,211; 8,731,132; 8,734,718; 8,748,111; 8,753,304; 8,771,343; 8,772,626; 8,779,277; 8,790,462; 8,790,614; 8,796,119; 8,796,417; 8,796,544; 8,815,273; 8,815,275; 8,840,863; 8,847,476; 8,864,341; 8,865,113; 8,871,670; 8,871,926; 8,878,157; 8,883,115; 8,884,507; 8,888,731; 8,900,292; 8,916,064; 8,920,491; 8,921,473; 8,927,615; 8,932,346; 8,936,734; 8,975,205; 8,993,089; 8,994,270; 9,004,131; 9,005,480; 9,018,122; 9,023,308; 9,040,145; 20030003300; 20030034486; 20040144726; 20040156986; 20040224147; 20050008861; 20050031876; 20050126338; 20050191492; 20050218397; 20050218398; 20050230822; 20050231855; 20050260269; 20050265935; 20050266697; 20050267345; 20060102468; 20060118493; 20060133975; 20060145326; 20060182997; 20060210798; 20060240386; 20060243321; 20060260674; 20070000407; 20070039814; 20070084507; 20070087187; 20070095389; 20070104629; 20070128707; 20070157967; 20070181508; 20070202334; 20070202342; 20070218049; 20070285843; 20080020127; 20080021212; 20080026041; 20080031806; 20080057420; 20080090930; 20080138267; 20080187684; 20080187724; 20080207581; 20080220535; 20080239791; 20080249600; 20080283411; 20080305045; 20080318044; 20090005880; 20090017303; 20090074649; 20090104369; 20090116277; 20090126604; 20090188407; 20090220600; 20090220698; 20090270997; 20090286936; 20090294692; 20090311513; 20100000874; 20100003204; 20100069229; 20100073995; 20100190639; 20100258446; 20100261263; 20100278720; 20100304204; 20100307593; 20100308286; 20100326699; 20110012096; 20110015300; 20110051220; 20110053285; 20110101862; 20110110141; 20110123409; 20110149400; 20110171789; 20110200761; 20110208021; 20110208023; 20110208026; 20110214996; 20110220855; 20110226738; 20110238001; 20110245074; 20110245576; 20110262312; 20110275912; 20110295088; 20110295089; 20110295090; 20110297846; 20120010314; 20120010481; 20120040581; 20120041285; 20120041286; 20120041287; 20120066926; 20120077006; 20120091429; 20120091482; 20120122652; 20120122668; 20120152336; 20120152337; 20120164561; 20120172648; 20120181163; 20120209090; 20120235094; 20120265122; 20120281428; 20120299175; 20120329657; 20130001067; 20130004778; 20130015076; 20130032470; 20130059396; 20130079577; 20130099196; 20130102458; 20130150809; 20130156905; 20130163310; 20130171060; 20130180862; 20130184144; 20130189607; 20130212789; 20130216774; 20130240758; 20130250403; 20130252798; 20140011013; 20140056947; 20140069819; 20140093744; 20140106471; 20140119026; 20140126269; 20140134092; 20140147398; 20140160723; 20140163303; 20140174905; 20140174906; 20140213427; 20140217330; 20140220091; 20140222117; 20140223997; 20140225498; 20140227211; 20140242389; 20140243934; 20140252275; 20140256534; 20140262743; 20140262806; 20140272030; 20140272623; 20140287237; 20140294721; 20140295102; 20140301904; 20140301905; 20140311221; 20140323946; 20140326311; 20140336039; 20140339072; 20140342254; 20140356574; 20150036234; 20150122639; 20150125829; each of which is expressly incorporated herein by reference.

What is claimed is:

1. A nanostructured ceramic coating having a thickness in excess of 100 nm, comprising titanium oxide nanostructures in an amorphous ceramic phase of titanium oxide or zinc oxide nanostructures in an amorphous ceramic phase of zinc oxide, comprising at least one of nanoparticles, nanoblades or nanorods precipitated or grown from an aqueous solution of a ceramic precursor directly on a surface of a polymeric substrate with a maximum temperature of 100° C. during the precipitation of the nanostructures.

2. The nanostructured ceramic coating according to claim 1, comprising titanium oxide.

3. The nanostructured ceramic coating according to claim 1, comprising zinc oxide.

4. The nanostructured ceramic coating according to claim 1, configured to be at least one of a photocatalytic coating, a photovoltaic coating, and a piezoelectric coating.

5. The nanostructured ceramic coating according to claim 1, wherein the substrate comprises an organic polymer.

6. The nanostructured ceramic coating according to claim 1, wherein the substrate comprises a polymeric substrate, and the surface comprises a conductive metalized coating between the polymeric substrate and the nanostructured titanium or zinc oxide ceramic coating, wherein the nanostructured titanium or zinc oxide ceramic coating is electrochemically deposited.

7. The nanostructured ceramic coating according to claim 1, deposited in a hydrothermal deposition process.

8. The nanostructured ceramic coating according to claim 1, wherein the aqueous solution of ceramic precursor is supersaturated.

9. The nanostructured ceramic coating according to claim 1, comprising at least one of an anatase phase and a rutile phase surrounded by amorphous titania.

10. The nanostructured ceramic coating according to claim 1, wherein the aqueous solution of titanium or zinc oxide ceramic precursor comprises at least one of $TiCl_4$, $Zn(Ac)_2$, and $Zn(NO_3)_2$.

11. The nanostructured ceramic coating according to claim 1, wherein the particles comprise nanorods or nanotubes.

12. A nanostructured ceramic coating comprising: a titanium or zinc oxide ceramic crystalline phase within a titanium or zinc oxide ceramic amorphous phase, together having a thickness in excess of 100 nm, formed by a precipitation of at least one of titanium dioxide and zinc oxide nanostructures from a supersaturated aqueous ceramic precursor solution directly onto a polymeric surface in a process having a maximum precipitation temperature below 100° C.

13. The nanostructured ceramic coating according to claim 12, wherein the surface is photocatalytic, and the nanostructured ceramic coating is configured contact a flow of aqueous solution, and to induce formation of free radicals in the aqueous solution under illumination.

14. The nanostructured ceramic coating according to claim 13, wherein the nanostructured ceramic coating comprises an exposed wetted surface of a washer having an aqueous washing fluid comprising the aqueous solution.

15. The nanostructured ceramic coating according to claim 13, wherein the nanostructured ceramic coating is deposited on an interior surface of a refrigerator.

16. The nanostructured ceramic coating according to claim 12, wherein the nanostructured ceramic coating is photocatalytic, in combination with:
an odor sensor; and
a control system, configured to control at least an illumination system configured to illuminate the nanostructured ceramic coating to induce formation of free radicals in an aqueous solution in contact with the nanostructured ceramic coating, in dependence on an output of the sensor.

17. The nanostructured ceramic coating according to claim 13, wherein the nanostructured ceramic coating is configured to produce biocidal products of moisture from sunlight.

18. A nanostructured ceramic coating having a thickness in excess of 100 nm, comprising photocatalytic crystalline, nanorod or nanotube ceramic nanostructures within an amorphous ceramic phase, formed directly on a polymeric surface from an aqueous solution of ceramic precursors at a temperature of less than 100° C. without damaging the polymeric surface.

19. The nanostructured ceramic coating according to claim 18, wherein the ceramic nanostructures are selected from the group consisting of titanium oxide and zinc oxide, formed by precipitation from the aqueous solution of ceramic precursor.

* * * * *